(12) United States Patent
Bennett et al.

(10) Patent No.: US 7,766,913 B2
(45) Date of Patent: Aug. 3, 2010

(54) BONE SHAPING INSTRUMENT AND METHOD FOR USING THE SAME

(75) Inventors: Travis Bennett, Huntington, IN (US); Joseph G. Wyss, Ft. Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1164 days.

(21) Appl. No.: 11/005,798

(22) Filed: Dec. 7, 2004

(65) Prior Publication Data
US 2006/0122616 A1 Jun. 8, 2006

(51) Int. Cl.
*A61F 5/00* (2006.01)
(52) U.S. Cl. .................................... 606/86 R
(58) Field of Classification Search ............. 606/86–89, 606/86 R; 409/177–179; 105/29.1
See application file for complete search history.

(56) References Cited

U.S. PATENT DOCUMENTS 5,312,411 A    5/1994   Steele et al.

(Continued)

FOREIGN PATENT DOCUMENTS

| DE | 103 09 987 | 9/2004 |
| EP | 0 337 901 | 10/1989 |
| WO | WO 96/07361 | 3/1996 |

OTHER PUBLICATIONS

"Advance: Unicompartmental Knee System", Wright Medical Technology, unknown date, (2 pages).

"Advance: Unicompartmental Knee System", Wright Medical Technology, Sep. 2003, (16 pages).

"Preservation: Uni-Compartmental Knee", DePuy a Johnson and Johnson Company, ©2002 DePuy Orthopaedics, (30 pages).

*Primary Examiner*—Thomas C Barrett
*Assistant Examiner*—James L. Swiger
(74) *Attorney, Agent, or Firm*—Maginot, Moore & Beck

(57) ABSTRACT

A bone resection tool for resecting an end of a bone along a surface having a curvature comprises a guide, a cutting tool and a track follower. The guide is configured to be removably attached in a fixed position to the end of the bone. The guide is configured to include a track exhibiting a curvature generally corresponding to the curvature of the surface to be resected in the bone. The cutting tool includes a cutting face. The track follower is configured to couple to the cutting tool and cooperate with the track to facilitate reciprocation of the cutting tool relative to the guide to induce the cutting face to resect the bone along the surface having the curvature. A method for cutting a bone along a curved surface conforming to the curvature of a curved surface of the underside of a prosthetic component comprises the steps of incising the tissue surrounding the surface of the bone, positioning a guide alongside the surface of a bone to be cut, affixing the guide to the bone, interconnecting a cutter having a cutting face with the guide, maintaining the cutting face generally parallel to the tangent of the curved surface and traversing the cutting face along the bone while guiding the cutter along the track. The tissue incision incises the tissue surrounding the surface of the bone to be cut in a minimally invasive fashion. The positioned guide includes a track configured to assimilate the curvature of the curved surface of the underside of the prosthetic component.

8 Claims, 14 Drawing Sheets

U.S. PATENT DOCUMENTS

| | | | |
|---|---|---|---|
| 5,496,324 A * | 3/1996 | Barnes | 606/79 |
| 5,810,827 A | 9/1998 | Haines et al. | |
| 6,673,077 B1 | 1/2004 | Katz | |
| 7,255,702 B2 * | 8/2007 | Serra et al. | 606/80 |
| 2004/0175247 A1 * | 9/2004 | VanderPol et al. | 409/132 |

* cited by examiner

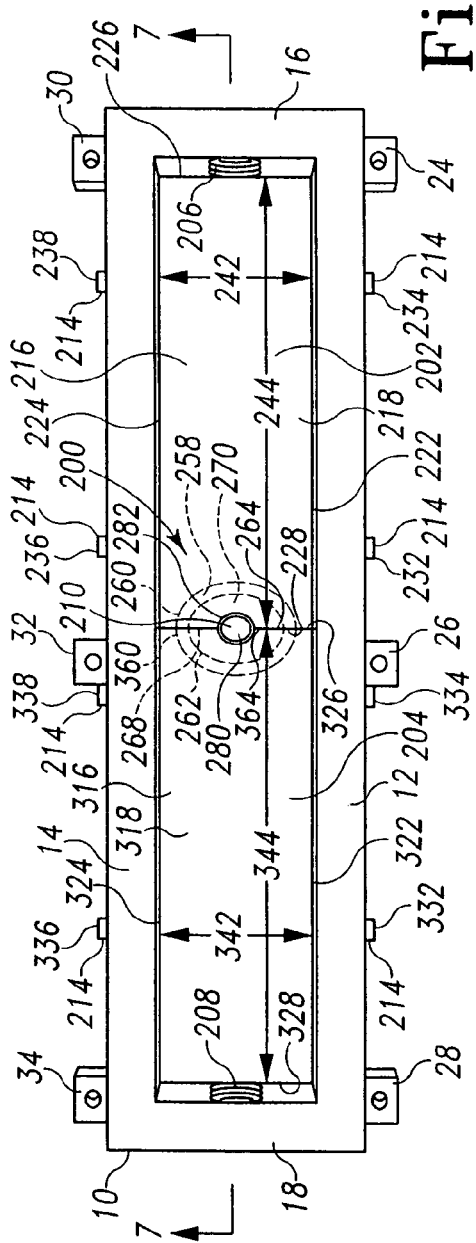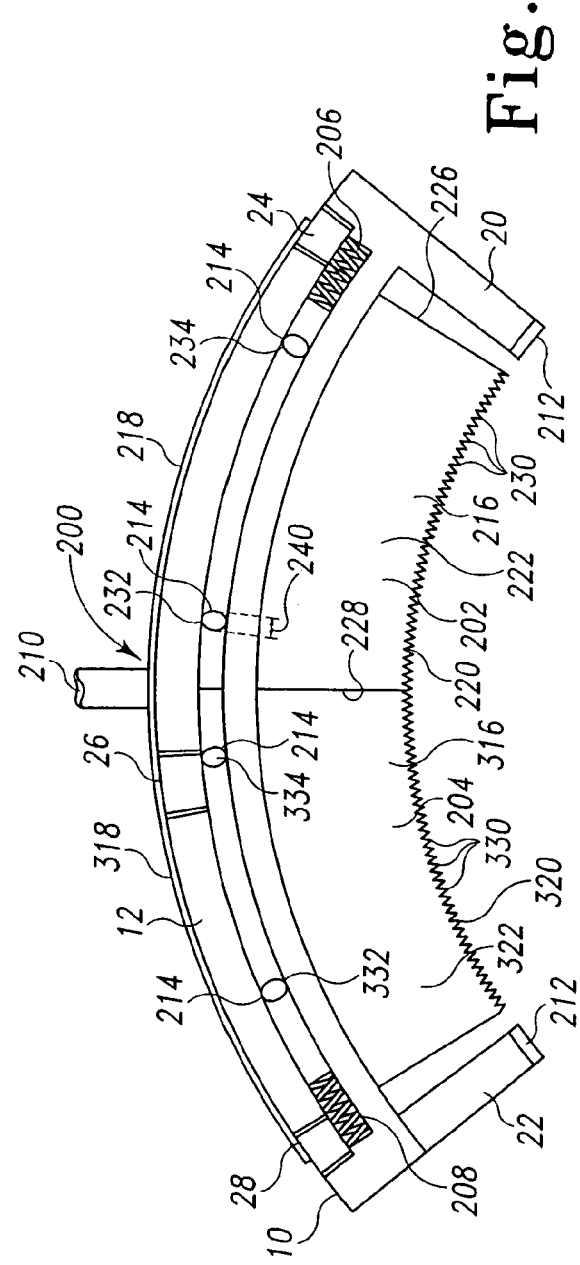

BONE SHAPING INSTRUMENT AND METHOD FOR USING THE SAME

FIELD OF THE INVENTION

This invention relates to joint arthroplasty and more particularly to tools and techniques for shaping a bone to receive a component of a joint replacement system.

BACKGROUND AND SUMMARY

It is well known to provide prosthetic joint components for replacing damaged and deteriorating joints. Typical joint replacements require resection of distal or proximal end of one or more of the bones forming the joint to be replaced to permit the prosthetic device to be firmly attached to the bone without altering the length of the limb in which the joint is being replaced. Joint component manufactures have recognized the benefits to be derived from joint replacement procedures that require less invasive surgeries with smaller incisions and more kinematically correct implants. Additionally, as younger patients are receiving joint replacements, there is a desire to provide joint replacements that allow the patient to recover from the replacement surgery more quickly, provide better function and are more durable.

One key to a kinematically correct durable implant is the interface between the bone and the implant. Due to the likelihood of eventual failure of a prosthesis there is always the possibility of the need for a replacement prosthetic procedures that will require further bone resections. Thus, it is preferable to resect a sufficient area of the bone to permit proper seating of the implant on the bone and to facilitate in-growth and/or on-growth of the bone to the implant, while reducing the amount of bone resected to allow further bone resections to accommodate revision or replacement of the implant. One method utilized to address the competing concerns of providing adequate bone resection to properly seat an implant and reducing the amount of bone resected to facilitate revision or replacement of the implant is to provide a surface replacement implant. Surface replacement implants require shaping the bone into curved or multiple non-coplanar surfaces rather than flat surfaces. It would be preferable to provide instruments for resecting the articulating surfaces of a bone to receive an implant that are minimally sized and that accurately guide a cutting tool to create curved surfaces for receipt of a surface replacement implant.

One type of surface implant in common use is the uni-compartmental knee system. The tibia (leg bone) and femur (thigh bone) meet at the knee and divide into medial (inner) and lateral (outer) tibio-femoral compartments. The patella (kneecap) in the front of the knee articulates with the trochlea (kneecap socket) of the femur to form the patello-femoral compartment. The tibio-femoral compartments are used for walking. The patello-femoral compartment is used for kneeling, squatting and stair-climbing. In unicompartmental knee arthroplasty, one of the knee's tibio-femoral compartments, usually the medial one, is resurfaced. This should be contrasted to total knee arthroplasty (TKA), which resurfaces both of the tibio-femoral compartments and usually the patello-femoral compartment. With the increased prevalence of unicompartmental knee arthroplasty (UKA), a prosthetic system which provides a conservative approach in terms of both instrumentation and implant design is important.

Age and activity level factor into all reconstructive procedures. Typically, the state of arthritis determines the treatment. With the advancement of minimally invasive techniques that support uni-compartmental knee reconstruction, a growing number of patients are offered this alternative for relief from the disabling pain of arthritis and for the potential benefits of a rapid recovery. Some patients have very significant arthritis changes in only one part of their knee, frequently on their inner or medial side. If there are no other major arthritis changes on the other side of the knee or under the knee cap, partial knee replacement (officially "uni-compartmental knee replacement") is indicated. Uni-compartmental knee replacement is a less invasive partial knee replacement procedure.

Benefits of uni-compartmental knee arthroplasty over total knee arthroplasty include 1) faster recovery, 2) less pain, 3) greater range of motion, 4) greater feeling of normalcy, 5) better alternatives when the prosthesis wears out, 6) no blood transfusions and 7) no need for blood thinners. Many of these benefits arise because with a uni-compartmental arthroplasty the surgery is less extensive, the incision is smaller, and there is less tissue trauma than in a TKA. A primary TKA will usually last 10-15 years. When it fails it must be replaced with a Revision TKA (RTKA). RTKAs have a high complication rate and don't last as long as primary TKAs. The uni-compartmental arthroplasty buys time. When it wears out it is replaced by a TKA. Patients may never need an RTKA or if they do, they generally will have gotten many more years use out of their TKA. By utilizing a uni-compartmental arthroplasty instead of a TKA, patients of any age can benefit. Older patients benefit from the reduced severity of the procedure and easier recovery. Younger patients benefit because when the prosthesis eventually fails (all prostheses fail faster in younger patients), they will be able to have it replaced with the better primary TKA as opposed to the less desirable RTKA.

Some prior art uni-compartmental knee systems have provided either limited instrumentation, making reproducible alignment difficult, or bulky instrumentation which requires more intrusive surgery. A few prior art uni-compartmental knee systems are designed with bone conserving femoral and tibial components that provide reproducible results utilizing a minimal incision. The resurfacing femoral implant conserves more quality bone stock compared to contemporary full resection femoral implants.

One such uni-compartmental knee system is the PRESERVATION™ Uni-compartmental Knee, available from DePuy Orthopaedics. The PRESERVATION™ Uni-compartmental Knee offers the surgeon fixed and mobile bearing tibial options specific to patient requirements. The system supports a less invasive procedure with instruments that provide for joint line restoration, load sharing balance, and component alignment. The PRESERVATION™ uni-compartmental knee system utilizes a technique that minimizes bone resections for later total knee arthroplasty options. The system is adapted to be utilized with Computer Aided Surgical ("CAS") technology.

The technical challenges of less invasive uni-compartmental knee surgery are becoming more apparent, even for the specialist arthroplasty surgeon. CAS technology has a clear role to play in less invasive surgery. CAS technology provides enhanced surgical vision which optimizes visualization of the critical anatomical landmarks, irrespective of the length of the incision. CAS technology offers the surgeon a level of vision and control that is difficult to achieve with non-CAS enabled, less invasive, procedures. With the key anatomy fully visualized, finger-tip instrument adjustment allows the surgeon to transfer on-screen planning to the table with greater precision. Virtual planning and kinematic assessment software provided with CAS technology allows implant positioning for each patient prior to any bone cuts being made.

The disclosed invention provides guides and a cutting tools configured to follow the guides to resect a bone to receive a surface replacement implant. The guide includes features to maintain the correct alignment of the cutting tool while providing sufficient freedom to create cuts having the desired depth for receiving a surface replacement prosthesis. The guides and cutting tools are configured to be effectively used in a minimal incision procedure while still offering the surgeon the alignment guides needed for consistent results. The disclosed guides are configured for utilization with CAS technology. Thus, reproducible outcomes are possible within a minimal incision.

According to one aspect of the disclosure, a bone resection tool for resecting an end of a bone along a surface having a curvature comprises a guide, a cutting tool and a track follower. The guide is configured to be removably attached in a fixed position to the end of the bone. The guide is configured to include a track exhibiting a curvature generally corresponding to the curvature of the surface to be resected in the bone. The cutting tool includes a cutting face. The track follower is configured to couple to the cutting tool and cooperate with the track to facilitate reciprocation of the cutting tool relative to the guide to induce the cutting face to resect the bone along the surface having the curvature.

According to another aspect of the disclosure, a method for cutting a bone along a curved surface conforming to the curvature of a curved surface of the underside of a prosthetic component comprises the steps of incising the tissue surrounding the surface of the bone, positioning a guide alongside the surface of a bone to be cut, affixing the guide to the bone, interconnecting a cutter having a cutting face with the guide, maintaining the cutting face generally parallel to the tangent of the curved surface and traversing the cutting face along the bone while guiding the cutter along the track. The tissue incision incises the tissue surrounding the surface of the bone to be cut in a minimally invasive fashion. The positioned guide includes a track configured to assimilate the curvature of the curved surface of the underside of the prosthetic component.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

The illustrative devices will be described hereinafter with reference to the attached drawings which are given as non-limiting examples only, in which:

FIG. 5 is a side view of the first embodiment of the guide of FIG. 1 and a second embodiment of a guided cutting tool including a posterior cutter, an anterior cutter and a driver of the bone shaping tool disclosed herein;

FIG. 6 is a top view of the guide and guided cutting tool of FIG. 5;

Corresponding reference characters indicate corresponding parts throughout the several views. Like reference characters tend to indicate like parts throughout the several views.

DETAILED DESCRIPTION

Figure 1:
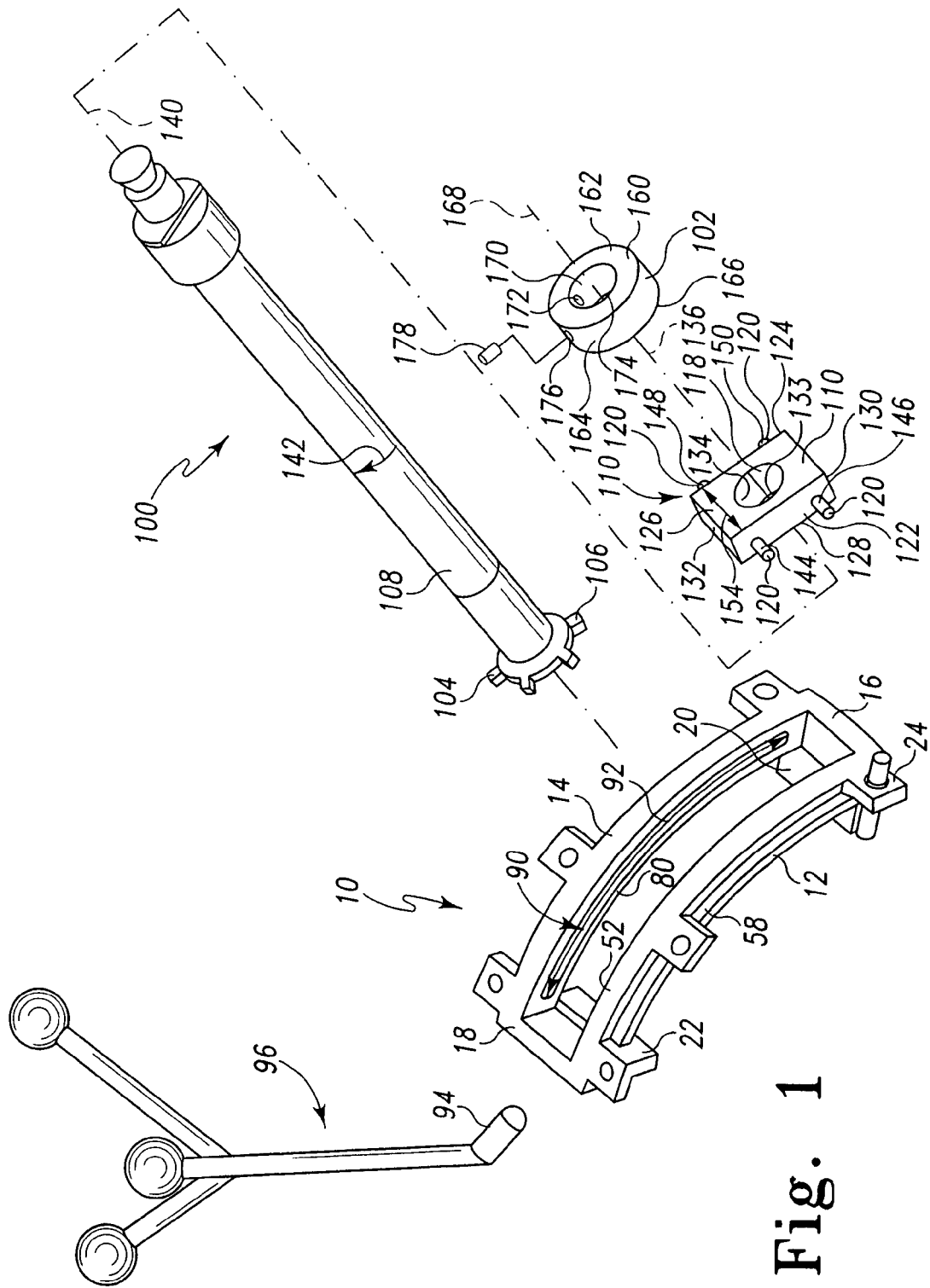
FIG. 1 is an exploded view of a first embodiment of a guide, a CAS orientation device and a first embodiment of a guided cutting tool including a cutter, a retaining collar and a depth stop of the bone shaping tool disclosed herein.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The disclosed bone shaping instruments facilitate preparation of a bone to receive a surface replacement implant such as a modified femoral component of a PRESENTATION™ uni-compartmental knee, available from DePuy Orthopedics, a Johnson & Johnson company modified to have an underside comprising a surface exhibiting a curvature. The instruments are described as being configured to prepare the distal femoral condyles or trochlea for knee arthroplasty. The instruments provide the options or preparing curved saggital and coronal cuts.

In one embodiment of the bone shaping instrument, an end and side cutting tool is translated within and guided by a tracked guide over a bone. The depth of the cut is controlled by a depth stop on the cutting tool engaging the guide and by the length of the legs of the guide which may be extendable or may be effectively extended using shims. The depth stop also controls the radius of curvature of the resection surface created by the instrument. Thus, if a deeper resection is required but the radius of curvature of the resected surface is not to be reduced, the depth of the resection should be adjusted by decreasing the length of the feet of the guide. However, if a deeper resection requiring a smaller radius of curvature is desired, the depth of the resection should be adjusted by moving the depth stop relative to the shaft of the cutting tool away from the cutting face of the cutting tool.

The depth stop is configured to be adjusted longitudinally with respect to the cutting tool to permit a surgeon to select the depth and the radius of curvature of the resection to be made. The depth stop and guide are configured to maintain the proper orientation of the cutting tool while it is being translated within the guide. In the illustrated embodiment the depth stop and guide are configured to maintain the cutting tool perpendicular to a guide track formed in the guide.

In a second embodiment of a cutting tool for use with the first embodiment of the guide, two rasps are configured to be driven by a hand drill while being guided by the guide. The rasps reciprocate on the surface of the bone creating the desired resection shape. Each of the cutting tools illustrated are configured to be driven by a flexible drive shaft to facilitate use of the bone shaping instrument in a surgical procedure utilizing minimally invasive incisions.

While only one size of each embodiment of the guide and each of the guided cutting tools are described in the disclosure, those skilled in the art will recognize that knee prosthesis systems typically include a plurality of differently sized femoral components and that for such a system a plurality of appropriately configured and sized guides and guided cutting tools could be provided. Thus, the disclosed guides and guided cutting tools will be described with reference to a femoral component of a uni-compartmental knee prosthesis system associated with the guide and guided cutting tool.

As shown, for example, generally in FIGS. 1-11 and more particularly in FIGS. 1-4, the first embodiment of the guide 10 includes a medial rail 12, a lateral rail 14, a posterior cross member 16, an anterior cross member 18, a posterior leg 19, an anterior leg 21, and a plurality of ears 24, 26, 28, 30, 32 and 34. The posterior cross member 16 extends between and couples the posterior end 36 of the medial rail 12 and the posterior end 38 of the lateral rail 14. The anterior cross member 18 extends between and couples the anterior end 40 of the medial rail 12 and the anterior end 42 of the lateral rail 14. The medial rail 12, lateral rail 14, posterior cross member 16 and anterior cross member 18 cooperate to define a tool-receiving slot 44 through which portions of the cutting tools 100, 200 and/or drive shafts 112 of the power source 114 extend to drive the cutting tools 100, 200.

In the illustrated embodiment, the medial rail 12 and the lateral rail 14 extend longitudinally parallel to one another to define the side walls of the tool-receiving slot 44. The medial rail 12 and the lateral rail 14 are spaced apart from one another by a displacement which also defines the width 46 of the tool-receiving slot 44. In one illustrated embodiment, the width 46 of the tool-receiving slot 44 is approximately thirteen millimeters to facilitate use in a minimally invasive procedure.

The posterior cross member 16 and anterior cross member 18 extend laterally parallel to one another to define the end walls of the tool-receiving slot 44. The posterior cross member 16 and anterior cross member 18 are spaced apart from one another by a displacement which also defines the length 48 of the tool-receiving slot 44.

Illustratively the medial rail 12 includes a concave bottom wall 50, a convex top wall 52, an inner wall 54 and an outer wall 56. The inner wall 54 and outer wall 56 are each flat and are generally parallel to one another. The inner wall 54 and outer wall 56 extend between and couple the concave bottom wall 50 and convex top wall 52. The concave bottom wall 50 and concave top wall 52 each exhibit a curvature that corresponds to the curvature of the underside of a femoral component of the uni-compartmental knee prosthesis associated with the particular guide 10.

The medial rail 12 is formed to include a curved slot 58 defined by a concave top wall 60, a convex bottom wall 62, a posterior wall 64 and an anterior wall 66, each of which extend between the inner wall 54 and the outer wall 56. The concave top wall 60 and convex bottom wall 62 each exhibit a curvature that corresponds to the curvature of the underside of a femoral component of the uni-compartmental knee prosthesis associated with the particular guide 10.

The concave top wall 60 and convex bottom wall 62 are spaced apart from one another by a displacement that serves as the width 68 of the curved slot 58. The width of the curved slot 58 is sized to capture guide pins 120, 214 therein for anterior-posterior longitudinal movement within the curved slot 58. The anterior wall 66 and posterior wall 64 of the curved slot 58 are spaced apart from one another by a displacement that serves as the length 70 of the curved slot 58. The anterior wall 66 and posterior wall 64 act as stops that limit the anterior-posterior longitudinal movement of guide pins 120, 214 when captured within the curved slot 58.

The medial rail 12 is formed to include a posterior medial ear 24, a central medial ear 26 and an anterior medial ear 28 extending outwardly from the outer wall 56. The posterior medial ear 24 is positioned adjacent the posterior end 36 of the medial rail 12. The anterior medial ear 28 is positioned adjacent the anterior end 40 of the medial rail 12. The central medial ear 26 is positioned near the middle of the medial rail 12 between the posterior medial ear 24 and the anterior medial ear 28. Each of the posterior medial ear 24, central medial ear 26 and anterior medial ear 28 are formed to include a fastener-receiving hole 29 configured to receive a fastener 31 for securing the guide 10 to the femur, as shown, for example, in FIGS. 8-11. The fastener-receiving holes 29 are formed concentrically about an axis that extends radially toward the focus of the center of curvature of the underside of a femoral component of the uni-compartmental knee prosthesis associated with the particular guide 10. The orientation of the fastener-receiving holes 29 facilitates insertion of the fasteners 31 through a minimally invasive incision to secure the guide 10 to the femur.

Illustratively, the medial rail 12 and the lateral rail 14 are formed symmetrically about a plane extending perpendicular to the rails 12, 14 through the center of the tool-receiving slot 44. Thus, the lateral rail 14 includes a concave bottom wall 72, a convex top wall 74, an inner wall 76 and an outer wall 78. The inner wall 76 and outer wall 78 are generally parallel to one another and extend between and couple the concave bottom wall 72 and convex top wall 74. The concave bottom wall 72 and concave top wall 74 each exhibit a curvature that corresponds to the curvature of the underside of a femoral component of the uni-compartmental knee prosthesis associated with the particular guide 10.

The lateral rail 14 is formed to include a curved slot 80 defined by a concave top wall 82, a convex bottom wall 84, a posterior wall 86 and an anterior wall 88 each of which extend between the inner wall 76 and outer wall 78. The concave top wall 82 and convex bottom wall 84 each exhibit a curvature that corresponds to the curvature of the underside of a femoral component of the uni-compartmental knee prosthesis associated with the particular guide 10. The concave top wall 82 and convex bottom wall 84 are spaced apart from one another by a displacement that serves as the width 90 of the curved slot 80. The width 90 of the curved slot 80 is sized to capture a guide pin 120, 214 therein for anterior-posterior longitudinal movement within the curved slot 80. The anterior wall 88 and posterior wall 86 of the curved slot 80 are spaced apart from one another by a displacement that serves as the length 92 of the curved slot 80. The anterior wall 88 and posterior wall 86 act as stops that limit the anterior-posterior longitudinal movement of guide pins 120, 214 when captured within the curved slot 80.

The lateral rail 14 is formed to include a posterior lateral ear 30, a central lateral ear 32 and an anterior lateral ear 34 extending outwardly from the outer wall 78. The posterior lateral ear 30 is positioned adjacent the posterior end 38 of the lateral rail 14. The anterior lateral ear 34 is positioned adjacent the anterior end 42 of the lateral rail 14. The central lateral ear 32 is positioned near the middle of the lateral rail 14 between the posterior lateral ear 30 and the anterior lateral ear 32. Each of the posterior lateral ear 30, central lateral ear 32 and anterior lateral ear 34 are formed to include a fastener-receiving hole 29 configured to receive a fastener 31 for securing the guide 10 to the femur.

The posterior leg 19 extends radially inwardly from the bottom surface of the posterior cross member 16 of the guide 10 terminating in a posterior foot 20. The anterior leg 21 extends radially inwardly from the bottom surface of the anterior cross member 18 of the guide 10 terminating in an anterior foot 22. The posterior foot 20 and the anterior foot 22 are configured to engage a condyle of the femur, or a shim 212, as described hereafter with reference to the second guided cutter 200, when the guide 10 is positioned for resection of the condyle. The posterior leg 19 and anterior leg 21 cooperate to displace the concave bottom wall 50 of the medial rail 12 and the concave bottom wall 72 of the lateral rail 14 from the condyle of the femur when the posterior and anterior feet 20, 22, respectively, engage the condyle or a shim 212. Since the effective length of the posterior leg 19 and the anterior leg 21 control the depth of the resection, they may be configured to be extendable and retractable if shim usage is not desired. Alternatively, a plurality of guides 10 may be provided each having posterior legs 19 and anterior legs 21 of varying lengths.

Figure 4:
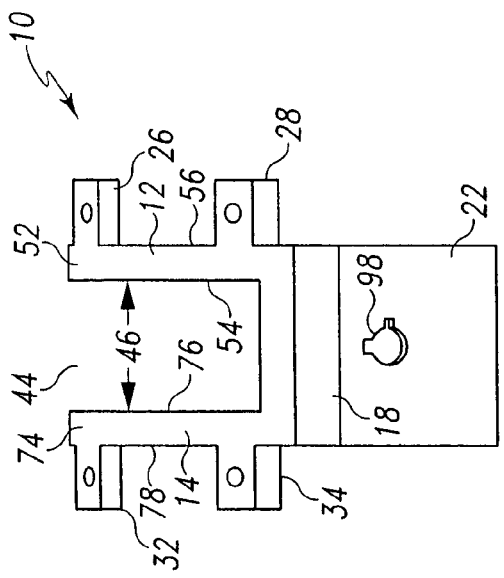
FIG. 4 is an end view of the guide of FIG. 3.
Figure 3:
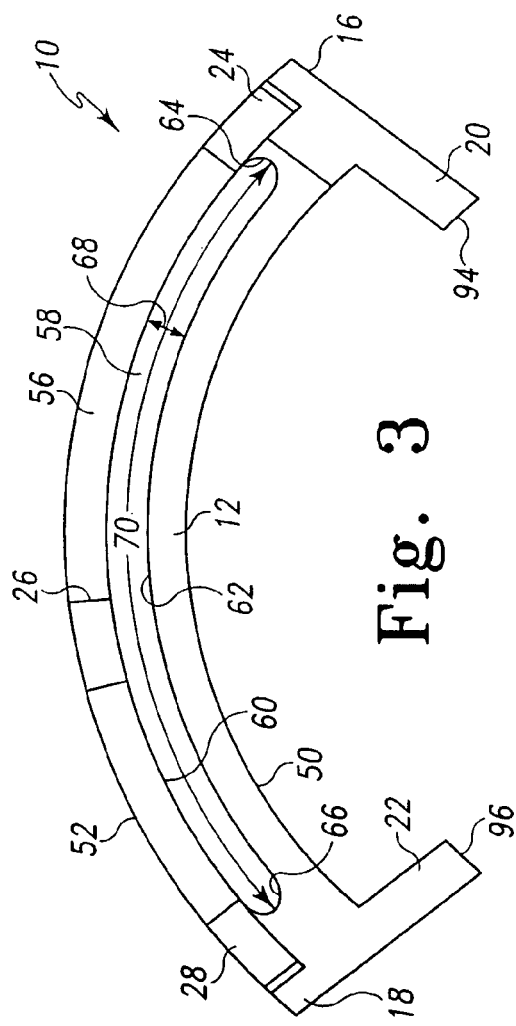
FIG. 3 is side elevation view of the guide of FIG. 2.
Figure 2:
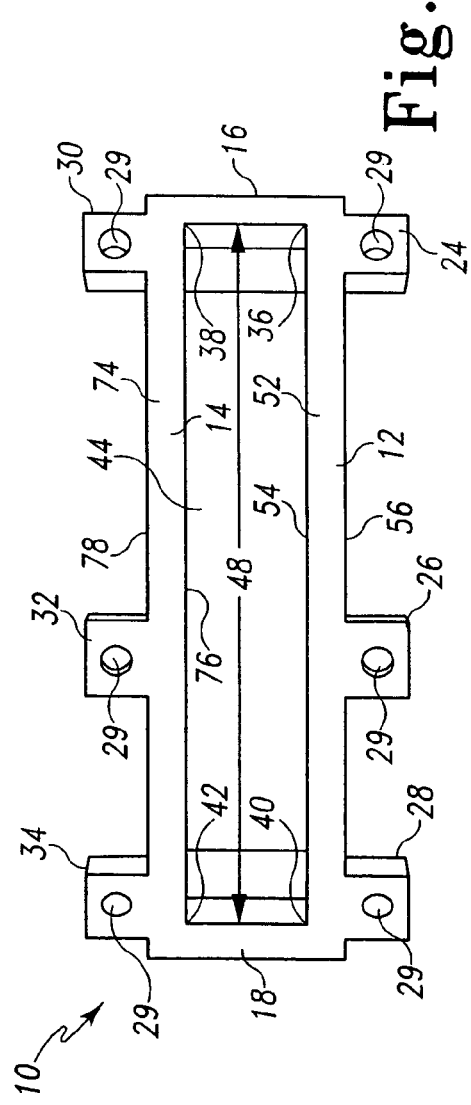
FIG. 2 is a top plan view of the guide of the bone shaping tool of FIG. 1.
Figure 8:
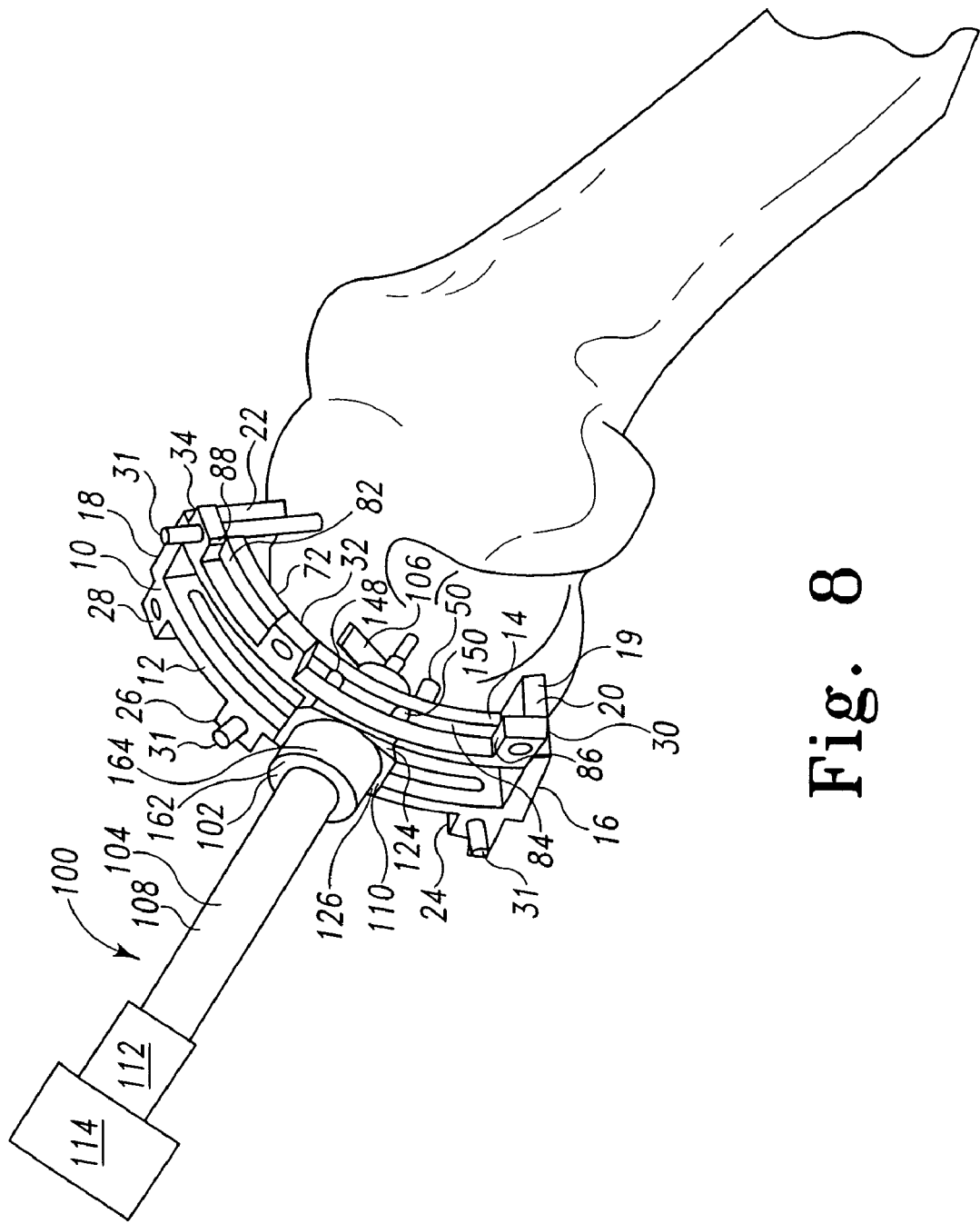
FIG. 8 is a perspective view of a the bone shaping tool of FIG. 1 pinned to the medial condyle on the distal end of a femur of a patient.
Figure 9:
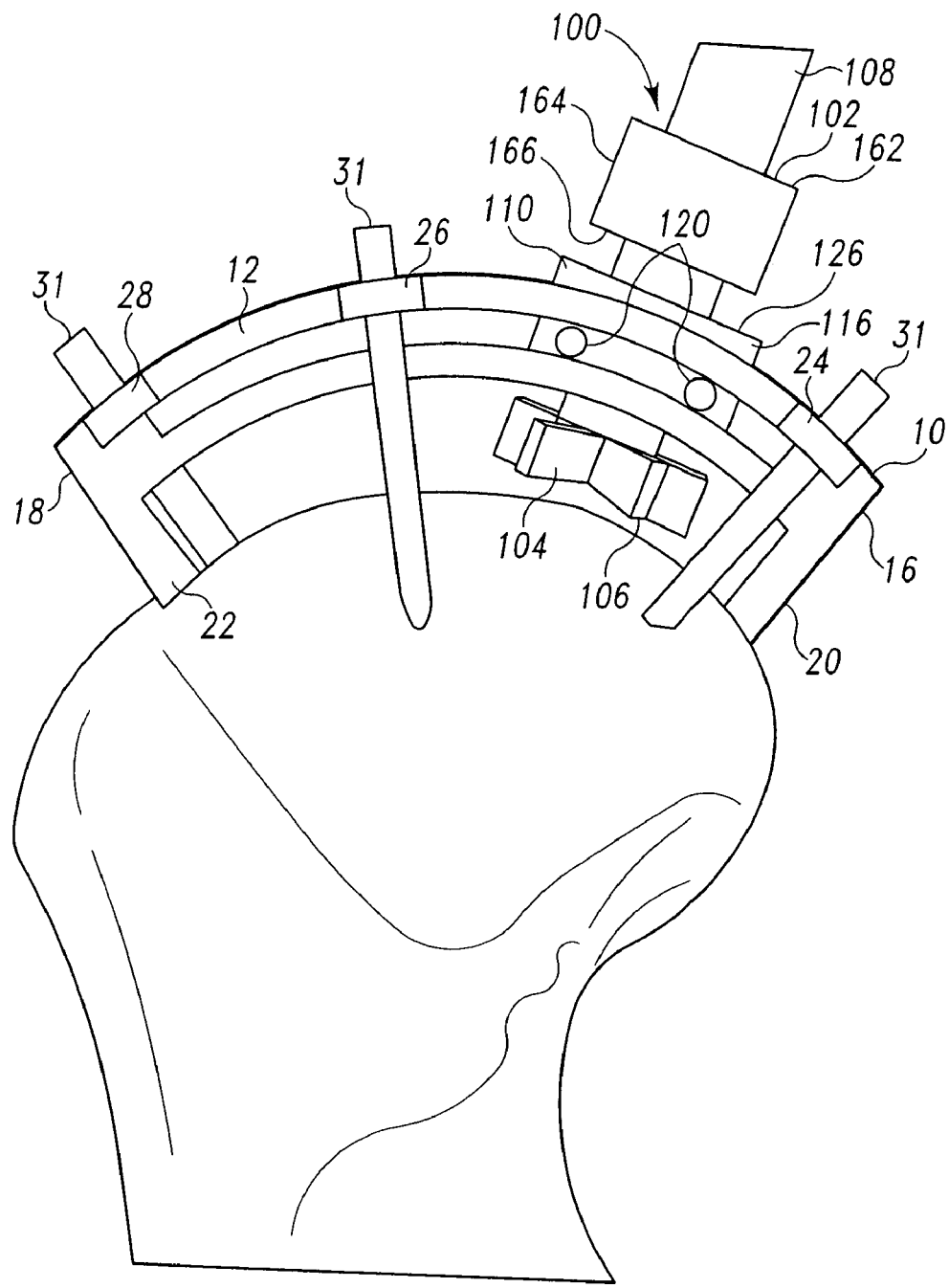
FIG. 9 is a side elevation view of the bone shaping tool of FIG. 8 showing the first embodiment of the guided cutting tool received in the guide prior to beginning resection of the medial condyle of the femur.
Figure 10:
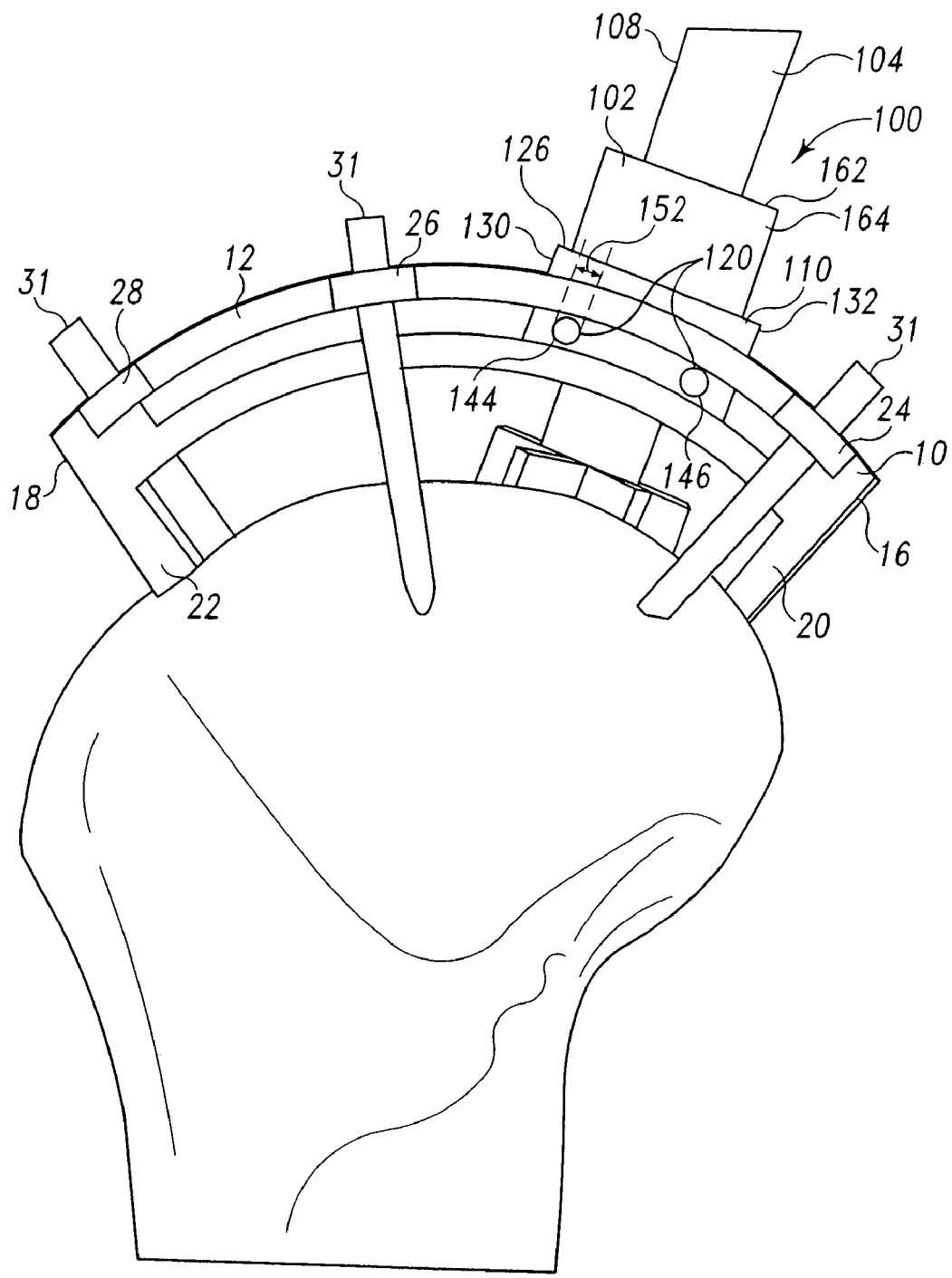
FIG. 10 is a side elevation view similar to FIG. 9 showing the guided cutting tool inserted into the medial condyle of the femur to the desired depth of the resection after being plunged into the femur from the position shown in FIG. 9.
Figure 11:
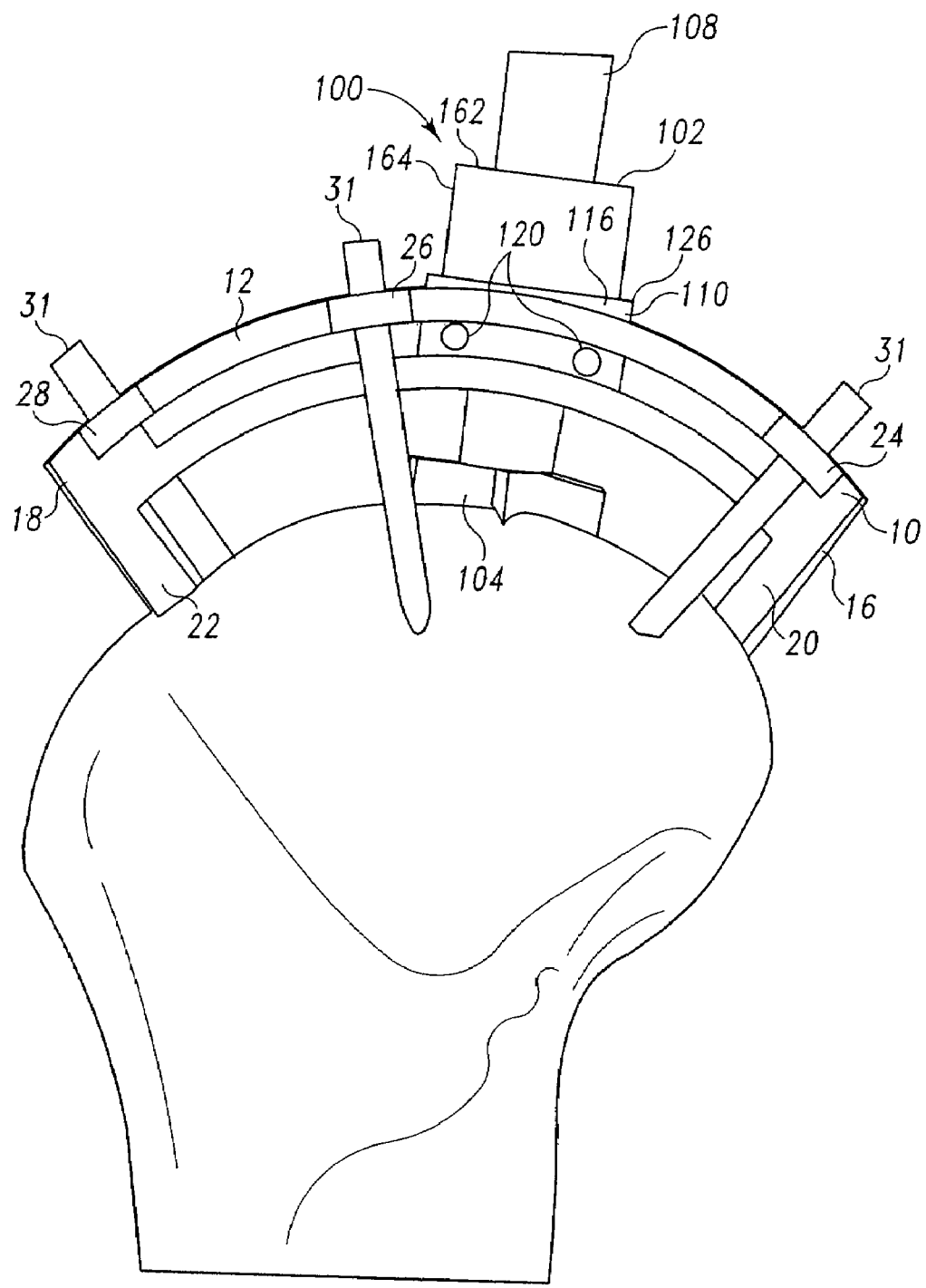
FIG. 11 is a side elevation view similar to FIG. 10 showing the guided cutting tool inserted into the medial condyle of the femur to the desired depth of the resection after being translated anteriorly guided by the guide.

As shown, for example, in FIGS. 1, 4 and 8, the anterior leg 21 is formed to include an aperture 98 sized and configured to receive a shaft 94 of a CAS orientation device 96 in a fixed orientation. When the shaft 94 of the CAS orientation device 96 is received in the aperture 98, the orientation device 96 provides details of the orientation of the guide 10 in three dimensions. Thus, when the CAS orientation device 96 is received in the aperture 98, CAS techniques may be utilized to ensure the proper positioning of the guide 10. Those skilled in the art will recognize that other couplings in different locations can be provided for attaching a CAS orientation device 96 to the guide 10 within the scope of the disclosure.

The first embodiment of a guided cutting tool 100 includes a depth stop 102, a cutter 104 and a retaining collar 110. The cutter 104 includes a cutting face 106 and a shaft 108. Illustratively, the cutter 104 includes a cutting face 106 that provides for end and side cutting. Cutter 104 may be a reamer, such as a concave spherical, convex spherical or planar reamer, an end mill or a burr. The cutting face 106 is mounted to the shaft 108 to be rotated about the longitudinal axis 140 of the shaft 108 when the shaft 108 is turned.

Illustratively, the shaft 108 is configured to be coupled to a drive shaft 112 of a power source 114. The power source 114 may be a hand drill with a rigid, or preferably flexible, drive shaft 112. The hand drill may be manually, electrically, pneumatically or hydraulically powered. It is within the scope of the disclosure for the power source 114 to be some other device configured to rotate the shaft 108 of the cutter 104.

The retaining collar 110 includes a body 116 formed to include a shaft-receiving aperture 118 and a plurality of guide pins 120. The body 116 of the retaining collar 110 includes parallel spaced apart side walls 122, 124 extending between and coupling a top wall 126 to a bottom wall 128 and an anterior wall 130 to a posterior wall 132. The top wall 126 is planar and is configured to act as a stop surface against which the depth stop 102 engages to limit the depth of the cut of the cutter 104. The shaft-receiving aperture 118 extends through the top wall 126 and the bottom wall 128. Illustratively, the shaft-receiving aperture 118 is defined by a cylindrical side wall 134 formed concentrically about a longitudinal axis 136 normal to the top wall 126. The cylindrical side wall 134 has an inside diameter 138. Illustratively, the cylindrical side wall 134 is configured to receive the shaft 108 of the cutter 104 therein and is sized to permit the shaft 108 of the cutter 104 to rotate freely therein about its longitudinal axis 140. The cylindrical side wall 134 cooperates with the shaft 108 of the cutter 104, and with the retaining collar 110 and depth stop 102, to maintain the alignment of the cutter 104. Thus, the inside diameter 138 of the shaft-receiving aperture 118 is slightly larger than the outside diameter 142 of the shaft 108 of the cutter 104 to limit misalignment of the cutter 104. In the illustrated embodiment, the shaft 108 of the cutter 104 is aligned to extend radially to facilitate utilization of the bone shaping instrument through a minimally invasive incision.

In the illustrated embodiment, the plurality of guide pins 120 include an anterior medial guide pin 144 and a posterior medial guide pin 146 extending perpendicularly from the medial side wall 122 of the retaining collar 110 and an anterior lateral guide pin 148 and a posterior lateral guide pin 150 extending perpendicularly from the lateral side wall 124 of the retaining collar 110. The guide pins 120 define a plane parallel to the top wall 126 of the retaining collar 110. Illustratively, each of the plurality of guide pins 120 have a diameter 152 slightly less than the widths 68, 90 of the curved slots 58, 80 permitting the guide pins 120, when received in the curved slots 58, 80, to reciprocate anteriorly-posteriorly within the curved slots 58, 80. The guide pins 120 may be spring loaded to permit the guide pins 120 to be reciprocated along their longitudinal axis into and out of the body 116 of the retaining collar 110.

The medial side wall 122 and the lateral side wall 124 of the body 116 of the retaining collar 110 are spaced apart by a displacement 154. The displacement 154 between the medial side wall 122 and the lateral side wall is slightly less than, but approximately equal to, the width 46 of the tool-receiving slot 44 of the guide 10. In use, portions of the retaining collar 110 are received in the tool-receiving slot 44 of the guide 10 for reciprocal movement anteriorly and posteriorly within the tool-receiving slot 44. Portions of the medial side wall 122 are disposed adjacent the inner wall 54 of the medial rail 12 and portions of the lateral side wall 124 are disposed adjacent the inner wall 76 of the lateral rail 14. The medial side wall 122 of the retaining collar 110 and the inner wall 54 of the medial rail 12 and the lateral side wall 124 of the retaining collar 110 and the inner wall 76 of the lateral rail 12 cooperate to restrict rotation of the retaining collar 110 about the longitudinal axis 136 of the shaft-receiving aperture 118 when the retaining collar is received within the tool-receiving slot 44. Since rotation of the retaining collar 110 within the tool-receiving slot 44 is limited, the guide pins 120 are retained within the curved slots 58, 80.

Illustratively, guide pins 120 act as track followers configured to induce the retaining collar 110 to follow a path having a curvature conforming to the curvature of the convex bottom walls 62, 84 of the curved slots 58, 80. Those skilled in the art will recognize that other track following devices may be utilized within the scope of the disclosure including, but not limited to walls, bosses, ears, and flanges extending from the body 116 of the retaining collar 110 and configured to be received in and guided by the curved slots 58, 80 during anterior-posterior reciprocation within the curved slots 58, 80. Also, it is within the scope of the disclosure for the medial rail and lateral rail to be formed with a curved bottom wall and a curved top wall that act as tracks and the retaining collar to include track followers such as guide pins, walls, bosses, ears, and flanges extending from the body 116 and configured to follow the curved bottom wall and a curved top wall, as shown, for example, in FIG. 12.

In use, the guide pins 120, when captured within the curved slots 58, 80, ride on the convex bottom walls 62, 84 of the curved slots 58, 80 which define a curved guide surface or track. The concave top walls 60, 82 of the curved slots 58, 80 act to restrict the proximal and distal movement of the guide pins 120 relative to the guide 10. The guide pins 120 ride within the curved slots 58, 80 and act to restrict the cutting face 106 of the cutter 104 to move along a curvature approximating the curvature of an inner surface of a femoral component of the uni-compartmental knee prosthesis associated with the particular guide 10.

The illustrated depth stop 102 includes a cylindrical body 160 formed to include a planar circular top wall 162, a cylindrical outer wall 164 and a planar circular bottom wall 166 formed concentrically about an axis 168. A shaft-receiving aperture 170 extending between and through the top wall 162 and bottom wall 164 is defined by a cylindrical side wall 172 formed concentrically about the axis 168. Illustratively, the cylindrical side wall 172 is configured to receive the shaft 108 of the cutter 104 therein and is sized to permit the shaft 108 of the cutter 104 to reciprocate longitudinally along its longitudinal axis 140. Thus, the inside diameter 174 of the shaft-receiving aperture 170 is slightly larger than the outside diameter 142 of the shaft 108 of the cutter 104 to facilitate adjusting the position of the depth stop 102 along the shaft 108 of the cutter 104. A set screw-receiving hole 176 extends radially between and through the outer wall 164 and cylindrical side wall 172 of the body 160 of the depth stop 102. The set screw-receiving hole 176 is appropriately sized and threaded to receive a set screw 178 therein for tightening to secure the depth stop 102 in a fixed position relative to the shaft 108 of the cutter 104. Those skilled in the art will recognize that other configurations of the depth stop 102 may be utilized to permit the depth stop 102 to be temporarily or permanently affixed to the shaft 108 of the cutter 104.

The planar circular bottom wall 166 of the depth stop 102 cooperates with the planar top wall 126 of the retaining collar 110 to limit the proximal movement of the cutter 104 relative to the femur thereby limiting the depth of the resection performed by the cutter 104. The planar circular bottom wall 166 of the depth stop 102 also engages the planar top wall 126 of the retaining collar 110 to facilitate proper alignment of the longitudinal axis of the shaft 108 of the cutter 104 with the axis 136 of the retaining collar 110 thereby maintaining correct alignment of the cutting face 106 when at the full resection depth. The cylindrical side wall 134 of the retaining collar 110 also cooperates with the shaft 108 of the cutter 104, and with the retaining collar 110 and depth stop 102, to maintain the alignment of the cutter 104 at other depths.

Figure 7:
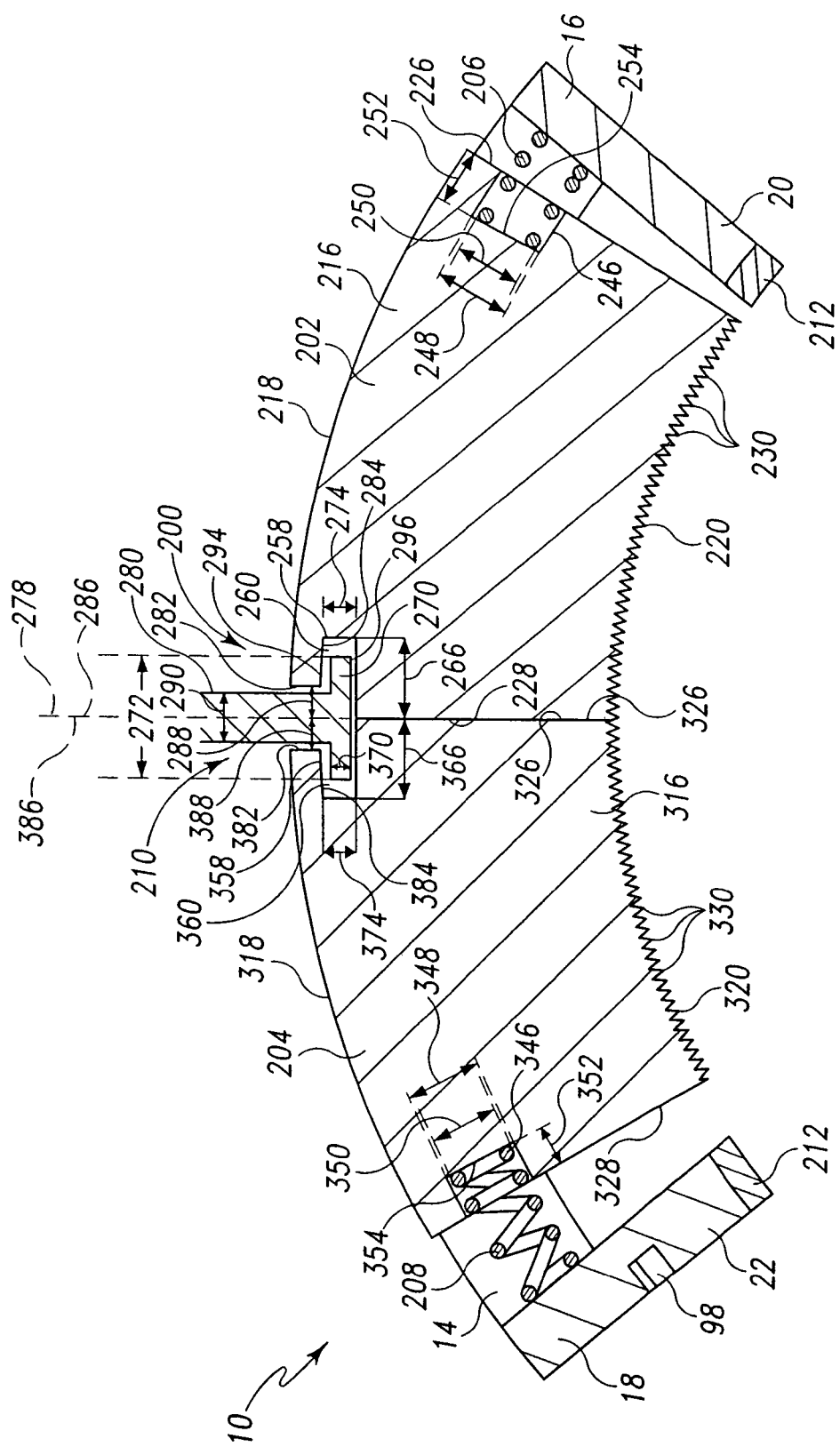
FIG. 7 is a sectional view taken along line 7-7 of the guide and guided cutting tool of FIG. 6.

As shown, for example, in FIGS. 5-7, the second embodiment of a guided cutting tool 200 includes a posterior cutter 202, an anterior cutter 204, a posterior return spring 206, an anterior return spring 208, a driver 210, a plurality of pairs of shims 212 and a plurality of guide pins 214. The plurality of pairs of shims 212 are provided for placing under the anterior foot 22 and posterior foot 20 of the guide 10 for adjusting the effective length of the posterior leg 19 and the anterior leg 21 and, thus, the depth of the resection performed by the guided cutting tool 200. The plurality of pairs of shims 212 will be provided in pairs having incrementally differing thickness to facilitate incrementally increasing the depth of the resection by replacing the shims 212 after the posterior and anterior cutters 202, 204 cease removing bone from the femur.

The posterior cutter 202 includes a body 216 having a top wall 218, a cutting surface 220, a medial side wall 222, a lateral side wall 224, a posterior end wall 226 and an anterior end wall 228. The medial side wall 222 and lateral side wall 224 extend between and couple the top wall 218 to the cutting surface 220 and the anterior end wall 228 to the posterior end wall 226.

In the illustrated embodiment, the top wall 218 and cutting surface 220 exhibit a posterior-anterior curvature that corresponds to the anterior-posterior curvature of the inner surface of a femoral component of the uni-compartmental knee prosthesis corresponding to the posterior cutter 202. Those skilled in the art will recognize that the curvature of the top wall 218 is not critical to the operation of the posterior cutter 202, but rather provides some aesthetic and possibly safety features to the cutter 202. Thus, it is within the scope of the disclosure for the top wall 218 to be flat or exhibit a different curvature than the cutting surface 220.

The cutting surface 220 is formed to include rows of teeth 230 extending medially-laterally across the cutting surface 220. The cutting surface 220, and its associated rows of teeth 230, may be medially-laterally flat or exhibit a concave or convex medial-lateral curvature to correspond to the medial-lateral curvature of a femoral component of the uni-compartmental knee prosthesis corresponding to the posterior cutter 202.

In the illustrated embodiment, the plurality of guide pins 214 include an anterior medial guide pin 232 and a posterior medial guide pin 234 extending perpendicularly from the medial side wall 222 of the posterior cutter 202 and an anterior lateral guide pin 236 and a posterior lateral guide pin 238 extending perpendicularly from the lateral side wall 224 of the posterior cutter 202. The plurality of guide pins 214 defines a plane parallel to a tangent of the cutting surface 220 of the posterior cutter 202. Illustratively, each of the plurality of guide pins 214 have a diameter 240 slightly less than the widths 68, 90 of the curved slots 58, 80 permitting the guide pins 214, when received in the curved slots 58, 80, to reciprocate anteriorly-posteriorly within the curved slots 58, 80. The guide pins 214 may be spring loaded to permit the guide pins 214 to be reciprocated along their longitudinal axis into and out of the body 216 of the posterior cutter 202.

The medial side wall 222 and the lateral side wall 224 of the body 216 of the posterior cutter 202 are parallel and spaced apart by a displacement 242. The displacement 242 between the medial side wall 222 and the lateral side wall 224 is slightly less than, but approximately equal to, the width 46 of the tool-receiving slot 44 of the guide 10. In use, portions of the posterior cutter 202 are received in the tool-receiving slot 44 of the guide 10 for reciprocal movement anteriorly and posteriorly within the tool-receiving slot 44. Portions of the medial side wall 222 are disposed adjacent the inner wall 54 of the medial rail 12 and portions of the lateral side wall 224 are disposed adjacent the inner wall 76 of the lateral rail 14. The medial side wall 222 of the posterior cutter 202 and the inner wall 54 of the medial rail 12 and the lateral side wall 224 of the posterior cutter 202 and the inner wall 76 of the lateral rail 12 cooperate to restrict rotation of the posterior cutter 202 with respect to the guide 10 when the posterior cutter 202 is received within the tool-receiving slot 44.

The posterior end wall 226 and the anterior end wall 228 of the body 216 of the posterior cutter 202 are spaced apart by a displacement 244. The displacement 244 between the posterior end wall 226 and the anterior end wall 228 is less than the half the length 48 of the tool-receiving slot 44 of the guide 10. In the illustrated embodiment, the posterior cutter 202 is configured to be driven by the driver 210 to reciprocate anteriorly-posteriorly within the tool-receiving slot 44 of the guide 10. The illustrated driver 210 is configured to induce the posterior cutter 202 to reciprocate anteriorly-posteriorly within the tool-receiving slot by a distance of approximately two millimeters. Thus, in the illustrated embodiment, the displacement 244 between the posterior end wall 226 and the anterior end wall 228 is approximately two millimeters less than the half the length 48 of the tool-receiving slot 44 of the guide 10.

As shown, for example, in FIG. 7, the posterior end wall 226 of the posterior cutter 202 is formed to include a bore 246 sized to receive portions of the posterior return spring 206. The bore 246 has a diameter 248 greater than the diameter 250 of the posterior return spring 206. The bore 246 has a depth 252 sufficient to prevent the posterior return spring 206 from dislodging from the bore 246 when received therein and compressed between the bottom wall 254 of the bore 246 and the posterior cross member 16 of the guide 10. The posterior return spring 206 is configured to return the posterior cutter 202 anteriorly to a central position within the guide 10 following posterior movement of the posterior cutter 202 relative to the guide 10. While not shown, it is within the scope of the disclosure for the posterior cross member 16 of the guide 10 to be configured to include a similar bore for receiving the opposite end of the posterior return spring 206.

As shown for example, in FIG. 7 and in phantom lines in FIG. 6, the anterior end wall 228 of the posterior cutter 202 is formed to include cavity 258 extending posteriorly into the body 216 of the posterior cutter 202. The cavity 258 includes a riding surface 260 for engaging the cam surface 262 of the driver 210. In the illustrated embodiment, the cavity 258 is a semi-elliptical cavity having its major axis 264 coplanar with the anterior end wall 228 and its semi-minor axis 266 perpendicular to the anterior end wall 228. The major axis 264 is slightly greater than the major axis 268 of the elliptical cam 270 of the driver 210 and the semi-minor axis 266 is approximately equal to half the minor axis 272 of the elliptical cam 270.

The cavity 258 has a height 274 slightly greater than the thickness 276 of the elliptical cam 270 of the driver 210 to capture the elliptical cam 270 within the cavity 258 for rotation therein. The riding surface 260 of the cavity 258 and the cam surface 262 of the driver 210 are configured so that rotation of the driver 210 about the longitudinal axis 278 of its shaft 280 induces reciprocal movement of the posterior cutter 202 within the guide 10 anteriorly and posteriorly by a distance equal to the difference between the major axis 268 and the minor axis 272 of the elliptical cam 270.

A semi-cylindrical groove 282 is formed in the anterior end wall 228 of the posterior cutter 202 extending between the cavity 258 and the top wall 218 of the posterior cutter 202. A semi-circular opening 284 is formed in the top wall 218 of the cavity 258 at the junction of the cavity 258 and the groove 282. A semi-circular opening is also formed in the top wall 218 of the posterior cutter 202 at the junction of the top wall 218 and the groove 282. The semi-cylindrical groove 282 is formed concentrically about an axis 286 coplanar with the anterior end wall 228, perpendicular to a tangent of the top wall 218 and parallel to the medial side wall 222 and lateral side wall 224. When the posterior cutter 202 and the anterior cutter 204 are both in their central positions within the guide 10, the semi-cylindrical groove 282 cooperates with a similar semi-cylindrical groove 382 in the anterior cutter 204 to receive the shaft 280 of the driver 210 therein for rotational movement about its longitudinal axis 278. Thus, the semicircular groove 282 has a radius 288 slightly greater than half the diameter 290 of the shaft 280 of the driver 210.

In the illustrated embodiment, the anterior cutter 204 is symmetrical to the posterior cutter 202. To reduce cutter components in the second embodiment of the cutting tool 200, a plurality of single cutters could be manufactured for orientation in opposite directions within the guide 10 to act as the anterior cutter 204 and posterior cutter 202.

The anterior cutter 204 includes a body 316 having a top wall 318, a cutting surface 320, a medial side wall 322, a lateral side wall 324, a posterior end wall 326 and an anterior end wall 328. The medial side wall 322 and lateral side wall 324 extend between and couple the top wall 318 to the cutting surface 320 and the anterior end wall 328 to the posterior end wall 326.

In the illustrated embodiment, the top wall 318 and cutting surface 320 exhibit a posterior-anterior curvature that corresponds to the anterior-posterior curvature of the inner surface of a femoral component of the uni-compartmental knee prosthesis corresponding to the anterior cutter 204. Those skilled in the art will recognize that the curvature of the top wall 318 is not critical to the operation of the anterior cutter 204, but rather provides some aesthetic and possibly safety features to the cutter 204. Thus, it is within the scope of the disclosure for the top wall 318 to be flat or exhibit a different curvature than the cutting surface 320.

The cutting surface 320 is formed to include rows of teeth 330 extending medially-laterally across the cutting surface 320. The cutting surface 320, and its associated rows of teeth 330, may be medially-laterally flat or exhibit a concave or convex medial-lateral curvature to correspond to the medial-lateral curvature of a femoral component of the uni-compartmental knee prosthesis corresponding to the anterior cutter 204.

In the illustrated embodiment, the plurality of guide pins 214 include an anterior medial guide pin 332 and a posterior medial guide pin 334 extending perpendicularly from the medial side wall 322 of the anterior cutter 204 and an anterior lateral guide pin 336 and a posterior lateral guide pin 338 extending perpendicularly from the lateral side wall 324 of the anterior cutter 204. The plurality of guide pins 214 defines a plane parallel to a tangent of the cutting surface 320 of the anterior cutter 204. Illustratively, each of the plurality of guide pins 214 have a diameter 240 slightly less than the widths 68, 90 of the curved slots 58, 80 permitting the guide pins 214, when received in the curved slots 58, 80, to reciprocate anteriorly-posteriorly within the curved slots 58, 80. The guide pins 214 may be spring loaded to permit the guide pins 214 to be reciprocated along their longitudinal axis into and out of the body 316 of the anterior cutter 204.

The medial side wall 322 and the lateral side wall 324 of the body 316 of the anterior cutter 204 are parallel and spaced apart by a displacement 342. The displacement 342 between the medial side wall 322 and the lateral side wall 324 is slightly less than, but approximately equal to, the width 46 of the tool-receiving slot 44 of the guide 10. In use, portions of the anterior cutter 204 are received in the tool-receiving slot 44 of the guide 10 for reciprocal movement anteriorly and posteriorly within the tool-receiving slot 44. Portions of the medial side wall 322 are disposed adjacent the inner wall 54 of the medial rail 12 and portions of the lateral side wall 324 are disposed adjacent the inner wall 76 of the lateral rail 14. The medial side wall 322 of the anterior cutter 204 and the inner wall 54 of the medial rail 12 and the lateral side wall 324 of the anterior cutter 204 and the inner wall 76 of the lateral rail 12 cooperate to restrict rotation of the anterior cutter 204 with respect to the guide 10 when the anterior cutter 204 is received within the tool-receiving slot 44.

The posterior end wall 326 and the anterior end wall 328 of the body 316 of the anterior cutter 204 are spaced apart by a displacement 344. The displacement 344 between the posterior end wall 326 and the anterior end wall 328 is less than the half the length 48 of the tool-receiving slot 44 of the guide 10. In the illustrated embodiment, the anterior cutter 204 is configured to be driven by the driver 210 to reciprocate anteriorly-posteriorly within the tool-receiving slot 44 of the guide 10. The illustrated driver 210 is configured to induce the anterior cutter 204 to reciprocate anteriorly-posteriorly within the tool-receiving slot 44 by a distance of approximately two millimeters. Thus, in the illustrated embodiment, the displacement 344 between the posterior end wall 326 and the anterior end wall 328 is approximately two millimeters less than the half the length 48 of the tool-receiving slot 44 of the guide 10.

As shown, for example, in FIG. 7, the anterior end wall 328 of the anterior cutter 204 is formed to include a bore 346 sized to receive portions of the anterior return spring 208. The bore 346 has a diameter 348 greater than the diameter 350 of the anterior return spring 208. The bore 346 has a depth 352 sufficient to prevent the anterior return spring 208 from dislodging from the bore 346 when received therein and compressed between the bottom wall 354 of the bore 346 and the anterior cross member 18 of the guide 10. The anterior return spring 208 is configured to return the anterior cutter 204 posteriorly to a central position within the guide 10 following anterior movement of the anterior cutter 204 relative to the guide 10. While not shown, it is within the scope of the disclosure for the anterior cross member 18 of the guide 10 to be configured to include a similar bore for receiving the opposite end of the anterior return spring 208.

As shown, for example, in FIG. 7 and in phantom lines in FIG. 6, the posterior end wall 326 of the anterior cutter 204 is formed to include cavity 358 extending anteriorly into the body 316 of the anterior cutter 204. The cavity 358 includes a riding surface 360 for engaging the cam surface 262 of the driver 210. In the illustrated embodiment, the cavity 358 is a semi-elliptical cavity having its major axis 364 coplanar with the posterior end wall 326 and its semi-minor axis 366 perpendicular to the posterior end wall 326. The major axis 364 is slightly greater than the major axis 268 of the elliptical cam 270 of the driver 210 and the semi-minor axis 366 is approximately equal to half the minor axis 272 of the elliptical cam 270.

The cavity 358 has a height 374 slightly greater than the thickness 276 of the elliptical cam 270 of the driver 210 to capture the elliptical cam 270 within the cavity 358 for rotation therein. The riding surface 360 of the cavity 358 and the cam surface 262 of the driver 210 are configured so that rotation of the driver 210 about the longitudinal axis 278 of its shaft 280 induces reciprocal movement of the anterior cutter 204 within the guide 10 anteriorly and posteriorly by a distance equal to the difference between the major axis 268 and the minor axis 272 of the elliptical cam 270.

A semi-cylindrical groove 382 is formed in the posterior end wall 326 of the anterior cutter 204 extending between the cavity 358 and the top wall 318 of the anterior cutter 204. A semi-circular opening 384 is formed in the top wall 318 of the cavity 358 at the junction of the cavity 358 and the groove 382. A semi-circular opening is also formed in the top wall 318 of the anterior cutter 204 at the junction of the top wall 318 and the groove 382. The semi-cylindrical groove 382 is formed concentrically about an axis 386 coplanar with the posterior end wall 326, perpendicular to a tangent of the top wall 318 and parallel to the medial side wall 322 and lateral side wall 324. When the posterior cutter 202 and the anterior cutter 204 are both in their central positions within the guide 10, the semi-cylindrical groove 382 cooperates with a similar semi-cylindrical groove 282 in the posterior cutter 202 to receive the shaft 280 of the driver 210 therein for rotational movement about its longitudinal axis 278. Thus, the semicircular groove 382 has a radius 388 slightly greater than half the diameter 290 of the shaft 280 of the driver 210.

The driver 210 includes an elliptical cam 270 and a shaft 280. Illustratively, the shaft 280 is formed concentrically about a longitudinal axis 278 and is configured to be coupled to the drive shaft 112 of the power source 114. The elliptical cam 270 includes a cam surface 262 extending between and coupling a top wall 294 and a bottom wall 296. The top wall 294 is displaced from the bottom wall 296 by the thickness 276 of the elliptical cam 270. The cam surface 262 has a major axis 268 and a minor axis 272. The shaft 280 of the driver 210 is coupled to the top wall 294 of the elliptical cam 270 with the longitudinal axis 278 of the shaft 280 extending perpendicularly from the intersection of the major axis 268 and minor axis 272 of the elliptical cam 270. The major axis 268 has a length that exceeds the length of the minor axis 272. In the illustrated embodiment, the major axis 268 is approximately four millimeters longer than the minor axis 272. Thus, when the driver 210 is rotated about the longitudinal axis 278 of its shaft 280, the cam surface 262 of the elliptical cam 270 engages the riding surfaces 260, 360 of the cavities 258, 358 to drive both the posterior cutter 202 and the anterior cutter 204 to each move approximately two millimeters anteriorly-posteriorly within the guide 10.

While not illustrated, the second embodiment of the cutting tool 200 may also include an alignment collar configured to be attached to the guide 10 to maintain the alignment of the shaft 280 of the driver 210 during rotation. Such alignment collar may include a body formed to include a shaft-receiving aperture and a plurality of pin holes. The pin holes may be formed in the body so that fasteners 31 extending through the fastener holes would also extend through the fastener-receiving holes 29 formed in the central medial ear 26 and central lateral ear 32 of the guide 10. The bottom wall of the alignment collar may be configured to contiguously engage the top walls of the lateral rail 14 and medial rail 12 to provide stability to the collar. The shaft-receiving aperture may be defined by a cylindrical side wall formed concentrically about a longitudinal axis. The cylindrical side wall of the alignment collar would be configured to receive the shaft 280 of the driver 210 therein and sized to permit the shaft 280 of the driver 210 to rotate freely therein about its longitudinal axis 278. The cylindrical side wall of the alignment collar would cooperate with the guide 10 to maintain the alignment and central position of the shaft 280 of the driver 210. Thus, the inside diameter of the shaft-receiving aperture of the alignment collar would be slightly larger than the outside diameter of the shaft 280 of the driver 210 to limit misalignment of the driver 210.

Illustratively, guide pins 214 act as track followers configured to induce the posterior cutter 202 and anterior cutter 204 to follow a path having a curvature conforming to the curvature of the convex bottom walls 62, 84 of the curved slots 58, 80. Those skilled in the art will recognize that other track following devices may be utilized within the scope of the disclosure including, but not limited to walls, bosses, ears, and flanges extending from the bodies 216, 316 of the posterior cutter 202 and anterior cutter 204, respectively, and configured to be received in and guided by the curved slots 58, 80 during anterior-posterior reciprocation within the curved slots 58, 80. Also, it is within the scope of the disclosure for the medial rail and lateral rail to be formed with a curved bottom wall and a curved top wall that act as tracks and the posterior cutter 202 and anterior cutter 204 to include track followers such as guide pins, walls, bosses, ears, and flanges extending from the body 216, 316 and configured to follow the curved bottom wall and a curved top wall that act as tracks.

In use, the guide pins 214, when captured within the curved slots 58, 80 of the guide 10, ride on the convex bottom walls 62, 84 of the curved slots 58, 80 which define a curved guide surface or track. The concave top walls 60, 82 of the curved slots 58, 80 act to restrict the proximal and distal movement of the guide pins 214 relative to the guide 10. The guide pins 214 ride within the curved slots 58, 80 and act to restrict the cutting surfaces 220, 320 of the posterior cutter 202 and anterior cutter 204, respectively, to move along a curvature approximating the curvature of an inner surface of a femoral component of the uni-compartmental knee prosthesis associated with the particular guide 10 and cutters 202, 204.

Figure 12:
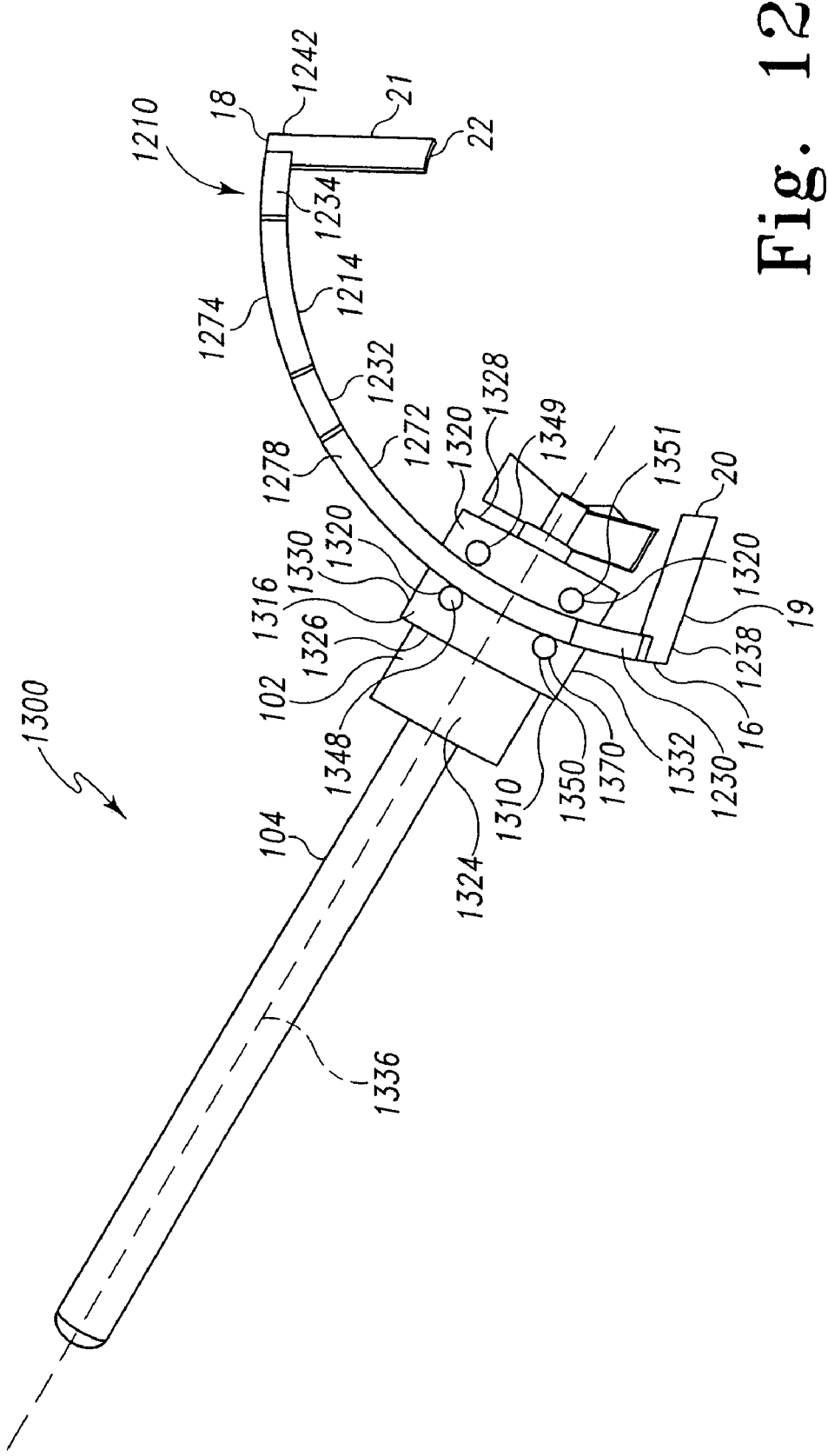
FIG. 12 is a side elevation view of a second embodiment of a guide and a third embodiment of a guided cutting tool similar wherein the medial and lateral side rails of the guide to guide two sets of four guide pins extending from the retainer collar.

An alternative embodiment of the bone shaping instrument comprising a second embodiment of a guide 1210 and a third embodiment of a cutting tool 1300 is shown, for example, in FIG. 12. The second embodiment of guide 1210 is very similar to the first embodiment of guide 10, so that identical reference numerals are used to identify identical components and similar reference numerals are used to identify similar components. Like guide 10, guide 1210 is formed symmetrically about a plane extending anteriorly to posteriorly through the tool-receiving slot. Thus, since FIG. 12 is a lateral side view of the guide 1210, only the lateral components will be described and identified by reference numerals, it being understood that the medial components are similarly formed. Guide 1210 includes a medial rail, a lateral rail 1214, a posterior cross member 16, an anterior cross member 18, a posterior leg 19, an anterior leg 21, and a plurality of ears 1230, 1232 and 1234. The posterior cross member 16 extends between and couples the posterior end of the medial rail and the posterior end of the lateral rail 1214. The anterior cross member 18 extends between and couples the anterior end of the medial rail and the anterior end of the lateral rail 1214. The medial rail, lateral rail 1214, posterior cross member 16 and anterior cross member 18 cooperate to define a tool-receiving slot through which portions of the cutting tool 1300 and/or drive shafts of the power source extend to drive the cutting tool 1300.

In the illustrated embodiment, the medial rail and the lateral rail 1214 extend longitudinally parallel to one another to define the side walls of the tool-receiving slot. The medial rail and the lateral rail 1214 are spaced apart from one another by a displacement which also defines the width of the tool-receiving slot. In one embodiment, the width of the tool-receiving slot is approximately thirteen millimeters to facilitate use in a minimally invasive procedure.

The posterior cross member 16 and anterior cross member 18 extend laterally parallel to one another to define the end walls of the tool-receiving slot. The posterior cross member 16 and anterior cross member 18 are spaced apart from one another by a displacement which also defines the length of the tool-receiving slot.

The lateral rail 1214 includes a concave bottom wall 1272, a convex top wall 1274, an inner wall and an outer wall 1278. The inner wall and outer wall 1278 are generally parallel to one another and extend between and couple the concave bottom wall 1272 and convex top wall 1274. The concave bottom wall 1272 and convex top wall 1274 each exhibit a curvature that corresponds to the curvature of the underside of a femoral component of the uni-compartmental knee prosthesis associated with the particular guide 1210.

The lateral rail 1214 is formed to include a posterior lateral ear 1230, a central lateral ear 1232 and an anterior lateral ear 1234 extending outwardly from the outer wall 1278. The posterior lateral ear 1230 is positioned adjacent the posterior end 1238 of the lateral rail 1214. The anterior lateral ear 1234 is positioned adjacent the anterior end 1242 of the lateral rail 1214. The central lateral ear 1232 is positioned near the middle of the lateral rail 1214 between the posterior lateral ear 1230 and the anterior lateral ear 1232. Each of the posterior lateral ear 1230, central lateral ear 1232 and anterior lateral ear 1234 are formed to include a fastener-receiving hole configured to receive a fastener 31 for securing the guide 1210 to the femur. The fastener-receiving holes are formed concentrically about an axis that extends radially toward the focus of the center of curvature of the underside of a femoral component of the uni-compartmental knee prosthesis associated with the particular guide 1210. The orientation of the fastener-receiving holes facilitates insertion of the fasteners 31 through a minimally invasive incision to secure the guide 1210 to the femur.

The third embodiment of the cutting tool 1300 is very similar to the first embodiment of the cutting tool 100, so that identical reference numerals are used to identify identical components and similar reference numerals are used to identify similar components. The third embodiment of a guided cutting tool 1300 includes a depth stop 102, a cutter 104 and a retaining collar 1310. Since only the retaining collar 1310 of cutting tool 1300 differs from the components of cutting tool 100, only the retaining collar 1310 will be described in detail, it being understood that the description of the depth stop 102 and cutter 104 of guided cutting tool 100 is applicable to the depth stop 102 and cutter 104 of guided cutting tool 1300.

The retaining collar 1310 includes a body 1316 formed to include a shaft-receiving aperture and a plurality of guide pins 1320. The body 1316 of the retaining collar 1310 includes parallel spaced apart side walls extending between and coupling a top wall 1326 to a bottom wall 1328 and an anterior wall 1330 to a posterior wall 1332. The top wall 1326 is planar and is configured to act as a stop surface against which the depth stop 102 engages to limit the depth of the cut of the cutter 104. The shaft-receiving aperture extends through the top wall 1326 and the bottom wall 1328. Illustratively, the shaft-receiving aperture is defined by a cylindrical side wall formed concentrically about a longitudinal axis 1336 normal to the top wall 1326. The cylindrical side wall has an inside diameter. Illustratively, the cylindrical side wall is configured to receive the shaft 108 of the cutter 104 therein and is sized to permit the shaft 108 of the cutter 104 to rotate freely therein about its longitudinal axis 140. The cylindrical side wall cooperates with the shaft 108 of the cutter 104, and with the retaining collar 1310 and depth stop 102, to maintain the alignment of the cutter 104. Thus, the inside diameter of the shaft-receiving aperture is slightly larger than the outside diameter of the shaft 108 of the cutter 104 to limit misalignment of the cutter 104. In the illustrated embodiment, the shaft 108 of the cutter 104 is aligned to extend radially to facilitate utilization of the bone shaping instrument through a minimally invasive incision.

In the illustrated embodiment, the plurality of guide pins 1320 include an upper anterior medial guide pin, a lower anterior medial guide pin, an upper posterior medial guide pin and a lower posterior medial guide pin extending perpendicularly from the medial side wall of the retaining collar 1310 and an upper anterior lateral guide pin 1348, a lower anterior lateral guide pin 1349, an upper posterior lateral guide pin 1350 and a lower posterior lateral guide pin 1351 extending perpendicularly from the lateral side wall 1324 of the retaining collar 1310. The guide pins 1320 define a plane parallel to the top wall 1326 of the retaining collar 1310. Illustratively, the upper anterior medial guide pin and upper posterior medial guide pin ride on the convex top wall of the medial rail and the lower anterior medial guide pin and lower posterior medial guide pin ride against the concave lower wall of the medial rail when the retaining collar 1310 is reciprocated posteriorly-anteriorly within the tool-receiving slot. The upper anterior lateral guide pin 1348 and upper posterior lateral guide pin 1350 ride on the convex top wall 1274 of the lateral rail 1214 and the lower anterior lateral guide pin 1349 and lower posterior lateral guide pin 1351 ride against the concave bottom wall 1272 of the lateral rail 1214 when the retaining collar 1310 is reciprocated posteriorly-anteriorly within the tool-receiving slot. The guide pins 1320 may be spring loaded to permit the guide pins 1320 to be reciprocated along their longitudinal axis into and out of the body 1316 of the retaining collar 1310.

The medial side wall and the lateral side wall 1324 of the body 1316 of the retaining collar 1310 are spaced apart by a displacement that is slightly less than, but approximately equal to, the width of the tool-receiving slot of the guide 1210. In use, portions of the retaining collar 1310 are received in the tool-receiving slot of the guide 1210 for reciprocal movement anteriorly and posteriorly within the tool-receiving slot. Portions of the medial side wall are disposed adjacent the inner wall of the medial rail and portions of the lateral side wall 1324 are disposed adjacent the inner wall of the lateral rail 1214.

Illustratively, guide pins 1320 act as track followers configured to induce the retaining collar 1310 to follow a path having a curvature conforming to the curvature of the concave bottom wall and convex top wall of the medial rail and the concave bottom wall 1272 and convex top wall 1274 of the lateral rail 1214. Those skilled in the art will recognize that other track following devices may be utilized within the scope of the disclosure including, but not limited to walls, bosses, ears, and flanges extending from the body 1316 of the retaining collar 1310 and configured to engage and be guided by the concave bottom wall and convex top wall of the medial rail and the concave bottom wall 1272 and convex top wall 1274 of the lateral rail 1214.

Figure 13:
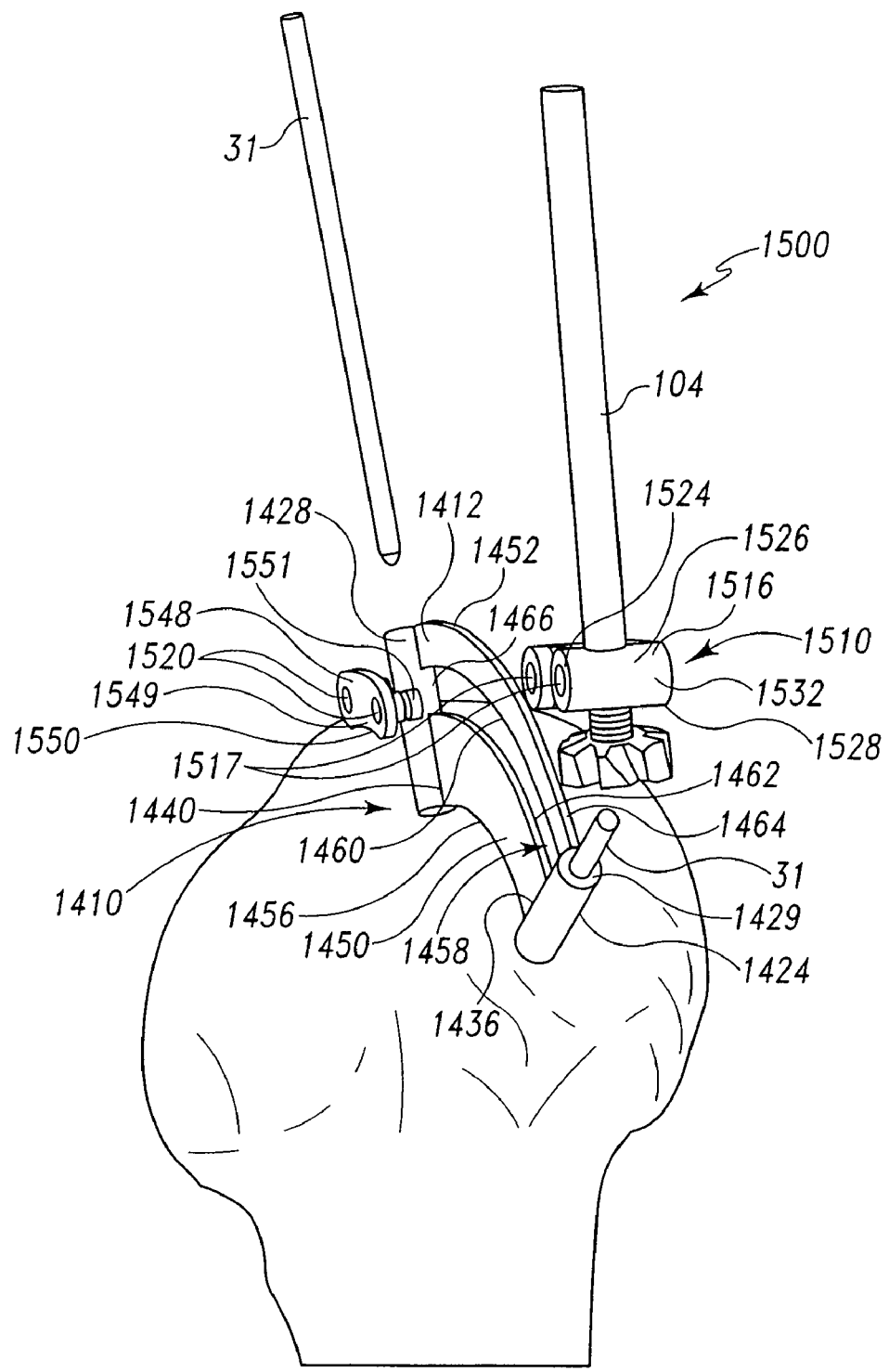
FIG. 13 is an exploded view of a third embodiment of a guide configured to include a guide channel, and a fourth embodiment of a guided cutting tool including a cutter, a retaining collar configured to receive guide pins configured to be captured in the guide channel of the guide of the bone shaping tool disclosed herein.
Figure 14:
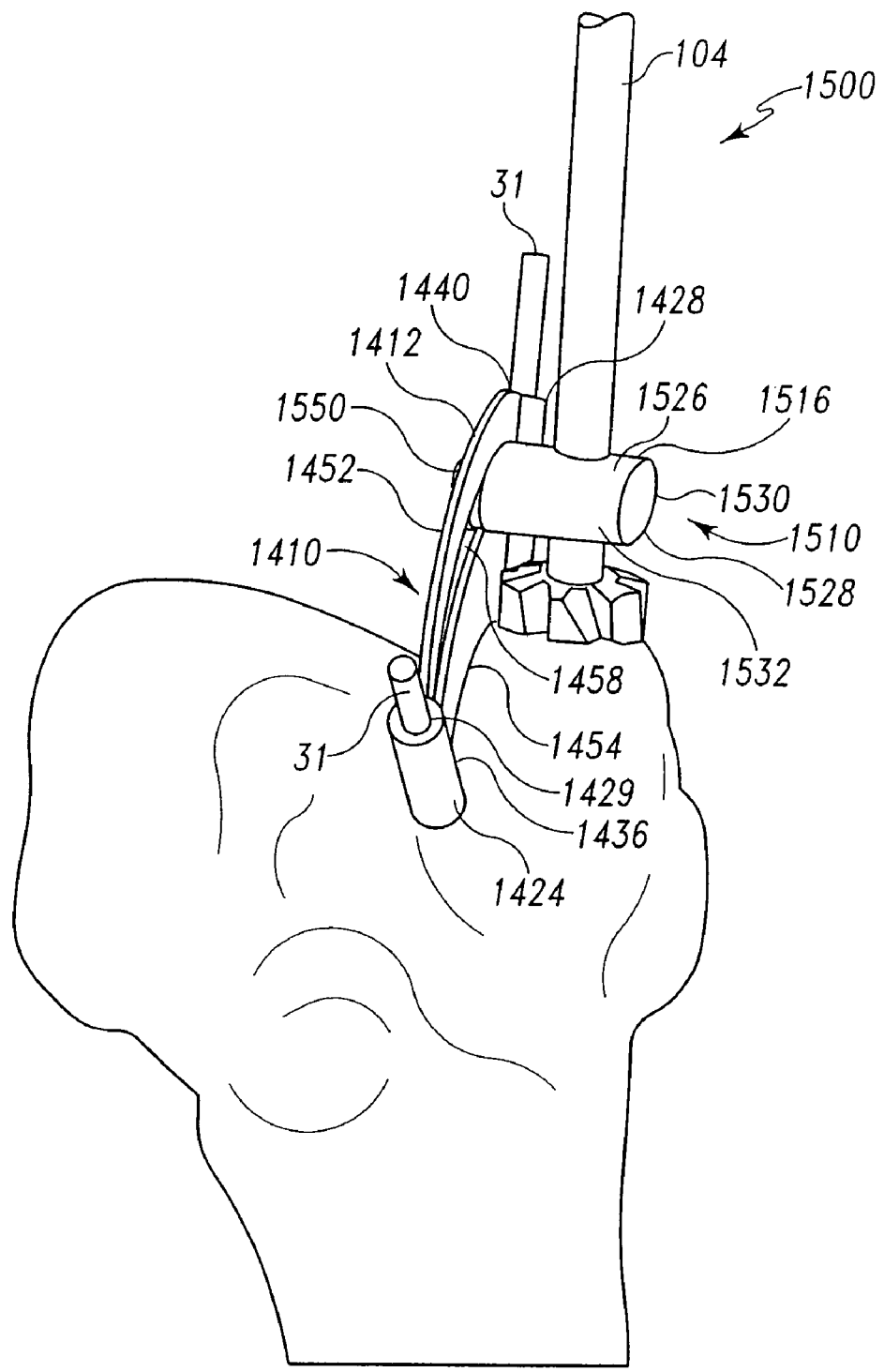
FIG. 14 is a perspective view of the third embodiment of a guide and the fourth embodiment of a guided cutting tool of FIG. 13 affixed to the bone to be resected.

Yet another alternative embodiment of the bone shaping instrument comprising a third embodiment of a guide 1410 and a fourth embodiment of a cutting tool 1500 is shown, for example, in FIGS. 13 and 14. Guide 1410 includes a guide plate 1412, an anterior pin-receiving cylinder 1428 and a posterior pin-receiving cylinder 1424.

Illustratively the guide plate 1412 includes a concave bottom wall 1450, a convex top wall 1452, an inner wall 1454 and an outer wall 1456. The inner wall 1454 and outer wall 1456 are each flat and are generally parallel to one another. The inner wall 1454 and outer wall 1456 extend between and couple the concave bottom wall 1450 and convex top wall 1452. The concave bottom wall 1450 and concave top wall 1452 each exhibit a curvature that corresponds to the curvature of the underside of a femoral component of the uni-compartmental knee prosthesis associated with the particular guide 1410.

The guide plate 1412 is formed to include a curved slot 1458 defined by a concave top wall 1460, a convex bottom wall 1462, a posterior wall 1464 and an anterior wall 1466, each of which extend between the inner wall 1454 and the outer wall 1456. The concave top wall 1460 and convex bottom wall 1462 each exhibit a curvature that corresponds to the curvature of the underside of a femoral component of the uni-compartmental knee prosthesis associated with the particular guide 1410.

The concave top wall 1460 and convex bottom wall 1462 are spaced apart from one another by a displacement that serves as the width of the curved slot 1458. The width of the curved slot 1458 is sized to capture guide pins 1520 therein for anterior-posterior longitudinal movement within the curved slot 1458. The anterior wall 1466 and posterior wall 1464 of the curved slot 1458 are spaced apart from one another by a displacement that serves as the length of the curved slot 1458. The anterior wall 1466 and posterior wall 1464 act as stops that limit the anterior-posterior longitudinal movement of guide pins 1520 when captured within the curved slot 1458.

The guide plate 1412 is formed to include a posterior pin-receiving cylinder 1424 and an anterior pin-receiving cylinder 1428. The posterior pin-receiving cylinder 1424 is coupled to the posterior end 1436 of the guide plate 1412. The anterior pin-receiving cylinder 1428 is coupled to the anterior end 1440 of the guide plate 1412. Each of the anterior pin-receiving cylinder 1428 and the posterior pin-receiving cylinder 1424 are formed to include a fastener-receiving hole 1429 configured to receive a fastener 31 for securing the guide 1410 to the femur. The fastener-receiving holes 1429 are formed concentrically about an axis that extends radially toward the focus of the center of curvature of the underside of a femoral component of the uni-compartmental knee prosthesis associated with the particular guide 1410. The orientation of the fastener-receiving holes 1429 facilitates insertion of the fasteners 31 through a minimally invasive incision to secure the guide 1410 to the femur.

The fourth embodiment of the cutting tool 1500 is very similar to the first embodiment of the cutting tool 100, so that identical reference numerals are used to identify identical components and similar reference numerals are used to identify similar components. The fourth embodiment of a guided cutting tool 1500 includes a cutter 104 and a retaining collar 1510. While not illustrated, those skilled in the art will recognize that the guided cutting tool 1500 may also include a depth stop 102. Since only the retaining collar 1510 of cutting tool 1500 differs from the components of cutting tool 100, only the retaining collar 1510 will be described in detail, it being understood that the description of the depth stop 102 and cutter 104 of guided cutting tool 100 is applicable to the depth stop 102 and cutter 104 of guided cutting tool 1500.

The retaining collar 1510 includes a body 1516 formed to include a shaft-receiving aperture and a plurality of threaded guide pin holes 1517 each configured to receive one of a plurality of guide pins 1520. The body 1516 of the retaining collar 1510 includes parallel spaced apart side walls extending between and coupling a top wall 1526 to a bottom wall 1528 and an anterior wall 1530 to a posterior wall 1532. The top wall 1526 is planar and is configured to act as a stop surface against which the depth stop 102 engages to limit the depth of the cut of the cutter 104. The shaft-receiving aperture extends through the top wall 1526 and the bottom wall 1528. Illustratively, the shaft-receiving aperture is defined by a cylindrical side wall formed concentrically about a longitudinal axis normal to the top wall 1526. The cylindrical side wall has an inside diameter. Illustratively, the cylindrical side wall is configured to receive the shaft 108 of the cutter 104 therein and is sized to permit the shaft 108 of the cutter 104 to rotate freely therein about its longitudinal axis 140. The cylindrical side wall cooperates with the shaft 108 of the cutter 104, and with the retaining collar 1510 and depth stop 102, to maintain the alignment of the cutter 104. Thus, the inside diameter of the shaft-receiving aperture is slightly larger than the outside diameter of the shaft 108 of the cutter 104 to limit misalignment of the cutter 104. In the illustrated embodiment, the shaft 108 of the cutter 104 is aligned to extend radially to facilitate utilization of the bone shaping instrument through a minimally invasive incision.

In the illustrated embodiment, the plurality of threaded guide pins 1520 includes an anterior guide pin 1548 and a posterior guide pin 1550. Each guide pin 1520 includes a head 1549 and a threaded shaft 1551 configured to be received in a guide pin-receiving hole 1517 in the body 1516. When so received, the guide pins 1520 extend perpendicularly from the outer side wall 1524 of the retaining collar 1510. The guide pins 1520 define a plane parallel to the top wall 1526 of the retaining collar 1510. When the guide pins 1520 are extended through the guide slot 1458 to couple the body 1516 of the retaining collar 1510 to the guide 1410, the inner walls of the heads 1549 of the guide pins 1520 are closely adjacent to, or in engagement with, the outer wall 1456 of the guide 1410. When so coupled to the guide 1410, the outer wall 1524 of the body 1516 is adjacent to, or in engagement with, the inner wall 1454 of the guide 1410. Illustratively, the anterior guide pin 1548 and the posterior guide pin 1550 ride on the convex bottom wall 1462 of the guide slot 1458 and the ride against the concave top wall 1460 of the guide slot 1458 when the retaining collar 1510 is reciprocated posteriorly-anteriorly. Thus, inner walls of the heads 1549 of the guide pins 1520 and the outer wall 1456 of the guide 1410, the outer wall 1524 of the body 1516 of the retaining collar 1510 and the inner wall 1454 of the guide 1410, the shafts 1551 of the guide pins 1520 and the convex bottom wall 1462 and concave top wall 1460 of the guide slot 1458 cooperate to maintain the proper alignment of the cutting tool 104 during resection of the bone.

Illustratively, guide pins 1520 act as track followers configured to induce the retaining collar 1510 to follow a path having a curvature conforming to the curvature of the concave top wall 1460 and convex bottom wall 1462 of the guide slot 1458. Those skilled in the art will recognize that other track following devices may be utilized within the scope of the disclosure including, but not limited to walls, bosses, ears, and flanges extending from the body 1516 of the retaining collar 1510 and configured to engage and be guided by the concave top wall 1460 and convex bottom wall 1462 of the guide slot 1458.

Figure 15:
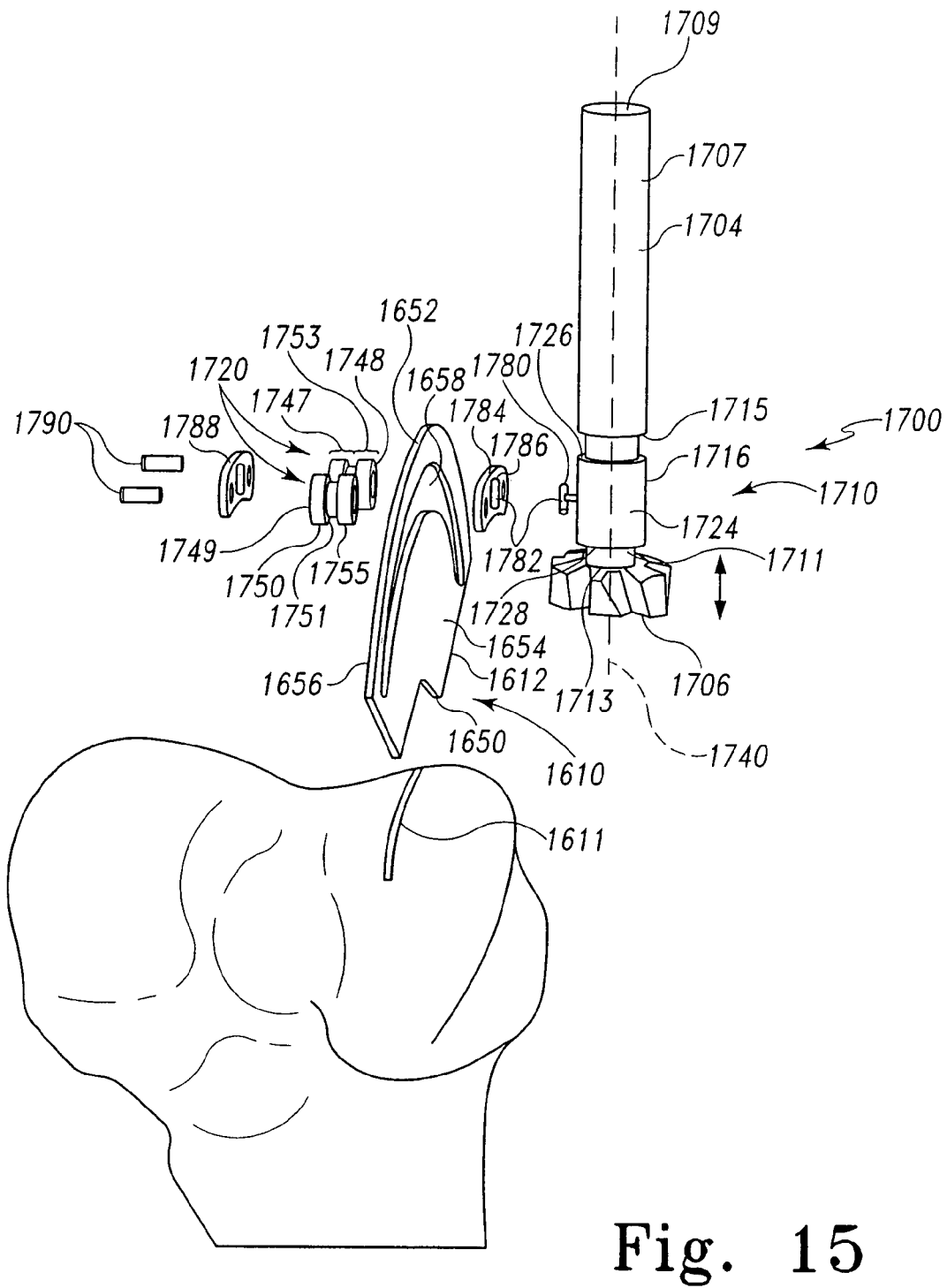
FIG. 15 is a perspective view of a fourth embodiment of a guide configured to be affixed to the bone to be resected by sliding into a slot formed in the bone and a fifth embodiment of a guided cutting tool of the bone shaping tool disclosed herein.
Figure 16:
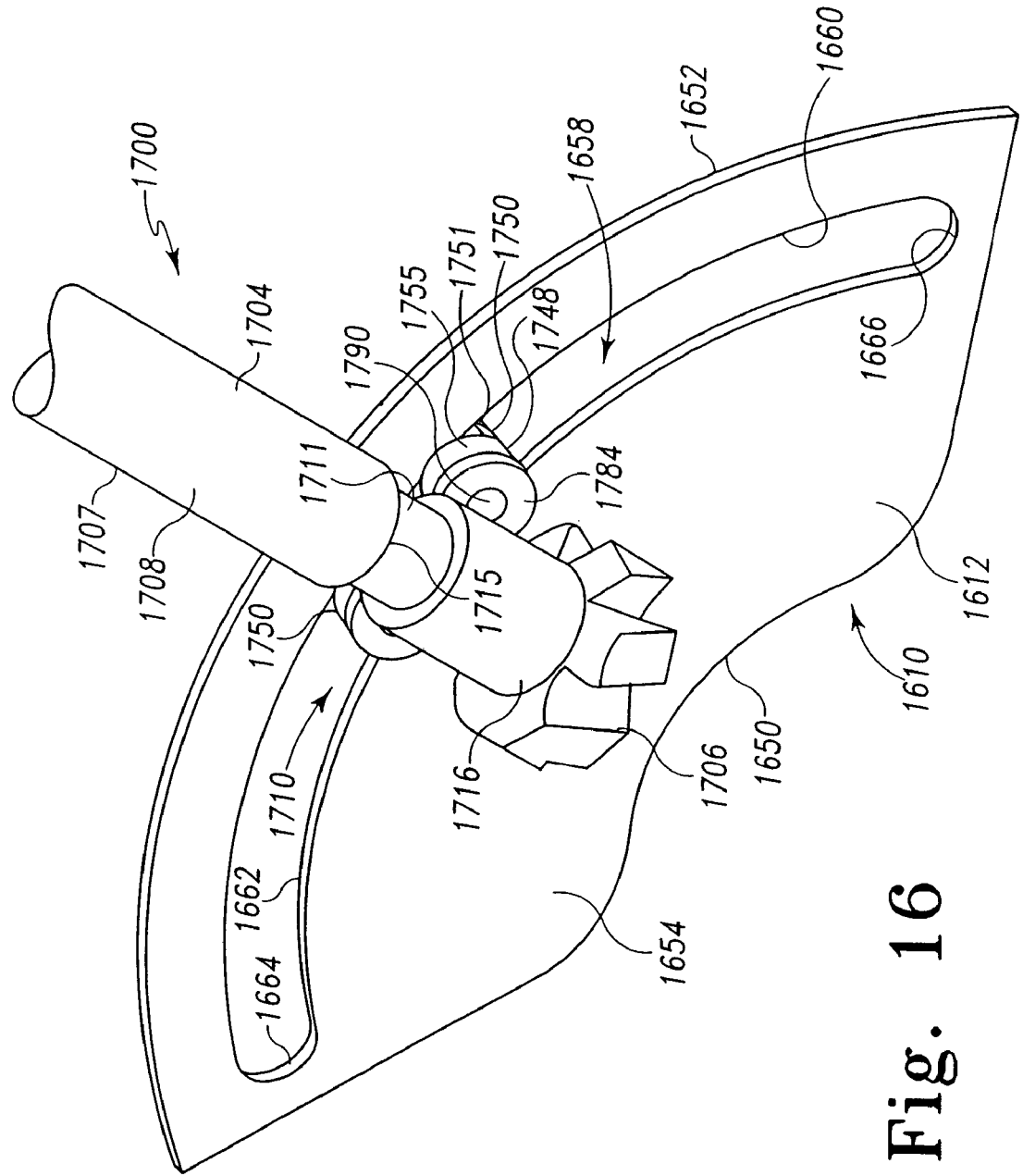
FIG. 16 is a perspective view of the fourth embodiment of the guide and fifth embodiment of the guided cutting tool of the bone shaping tool of FIG. 15.
Figure 17:
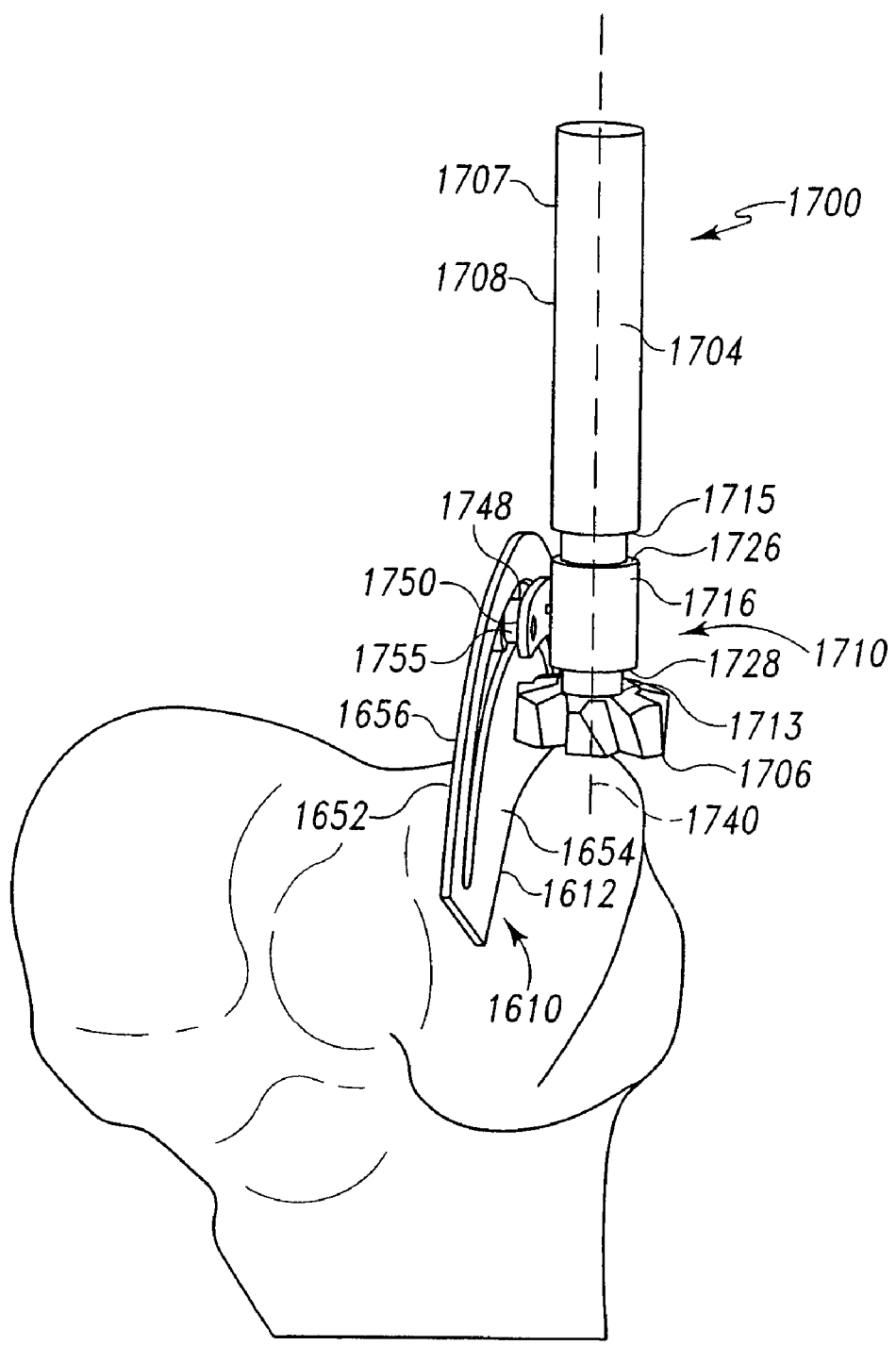
FIG. 17 is a perspective view of the fourth embodiment of the guide and fifth embodiment of the guided cutting tool of the bone shaping tool of FIG. 15 affixed to the bone to be resected.

Yet another alternative embodiment of the bone shaping instrument comprising a third embodiment of a guide 1610 and a fourth embodiment of a cutting tool 1700 is shown, for example, in FIGS. 15-17.

Guide 1610 includes a guide plate 1612 and is very similar to guide 1410 except for the lack of pin-receiving cylinders 1424 and 1428. Guide 1610 is intended to be attached to the bone to be resected by inserting guide 1610 into a resected slot 1611 formed in the bone at a desired location.

Illustratively the guide plate 1612 includes a concave bottom wall 1650, a convex top wall 1652, an inner wall 1654 and an outer wall 1656. The inner wall 1654 and outer wall 1656 are each flat and are generally parallel to one another. The inner wall 1654 and outer wall 1656 extend between and couple the concave bottom wall 1650 and convex top wall 1652. The concave bottom wall 1650 and concave top wall 1652 each exhibit a curvature that corresponds to the curvature of the underside of a femoral component of the uni-compartmental knee prosthesis associated with the particular guide 1610.

The guide plate 1612 is formed to include a curved slot 1658 defined by a concave top wall 1660, a convex bottom wall 1662, a posterior wall 1664 and an anterior wall 1666, each of which extend between the inner wall 1654 and the outer wall 1656. The concave top wall 1660 and convex bottom wall 1662 each exhibit a curvature that corresponds to the curvature of the underside of a femoral component of the uni-compartmental knee prosthesis associated with the particular guide 1610.

The concave top wall 1660 and convex bottom wall 1662 are spaced apart from one another by a displacement that serves as the width of the curved slot 1658. The width of the curved slot 1658 is sized to capture central shafts 1751 of guide bushings 1720 therein for anterior-posterior longitudinal movement within the curved slot 1658. The anterior wall 1666 and posterior wall 1664 of the curved slot 1658 are spaced apart from one another by a displacement that serves as the length of the curved slot 1658. The anterior wall 1666 and posterior wall 1664 act as stops that limit the anterior-posterior longitudinal movement of guide bushings 1720 when captured within the curved slot 1658.

The fifth embodiment of the cutting tool 1700 is very similar to the first embodiment of the cutting tool 100, so that identical reference numerals are used to identify identical components and similar reference numerals are used to identify similar components. The fifth embodiment of a guided cutting tool 1700 includes a cutter 1704 and a retaining collar 1710. Cutter 1704 is very similar to cutter 104 except that cutter 1704 is modular including a drive shaft 1708 formed to include a large diameter section 1707 adjacent the proximal end 1709 and a small diameter section 1711 adjacent the distal end 1713 and a cutting face 1706 configured for removable attachment to the distal end 1713 of the shaft 1708. The distal wall 1715 of the large diameter section 1707 of the shaft 1708 acts as a depth stop. The cutting face 1706 is removably attached to the shaft 1708 to facilitate mounting the retaining collar 1710 on the small diameter section 1711 of the shaft 1708 and to facilitate changing cutting faces 1706.

The retaining collar 1710 includes a body 1716 formed to include a shaft-receiving aperture and a male portion 1780 of a coupling 1782, a body plate 1784 formed to include a female portion 1786 of the coupling 1782, a plurality of modular guide bushings 1720, an outer plate 1788 and a plurality of fasteners 1790.

The small diameter section of the shaft 1708 extends through the shaft receiving aperture in the body 1716 to mount the retaining collar 1710 to the cutter 1704. The body 1716 includes a cylindrical side wall 1724 extending between and coupling a top wall 1726 and a bottom wall 1728. The top wall 1726 is planar and is configured to act as a stop surface against which the distal wall 1715 of the large diameter section 1707 of the shaft 1708 engages to limit the depth of the cut of the cutter 1704. The shaft-receiving aperture extends through the top wall 1726 and the bottom wall 1728. Illustratively, the shaft-receiving aperture is defined by a cylindrical side wall formed concentrically about a longitudinal axis normal to the top wall 1726. The cylindrical side wall has an inside diameter. Illustratively, the cylindrical side wall is configured to receive the small diameter section 1711 of the shaft 1708 of the cutter 1704 therein and is sized to permit the small diameter section 1711 of the shaft 1708 of the cutter 1704 to rotate freely therein about its longitudinal axis 1740. The cylindrical side wall cooperates with the small diameter section 1711 of the shaft 1708 of the cutter 1704 to maintain the alignment of the cutter 1704. Thus, the inside diameter of the shaft-receiving aperture is slightly larger than the outside diameter of the small diameter section 1711 of the shaft 1708 of the cutter 1704 to limit misalignment of the cutter 1704.

In the illustrated embodiment, the plurality of modular guide bushings 1720 includes a modular anterior guide bushing 1748 and a modular posterior guide bushing 1750. Each modular guide bushing 1720 includes a first portion 1747 having a head 1749 and a shaft 1751 and a second portion 1753 comprising a cap 1755. The shaft 1751 is configured to be received in a guide slot 1658 of the guide 1610.

The male portion 1780 of a coupling 1782 on the body 1716 is coupled to the female portion 1786 of the coupling 1782 on the body plate 1784 to couple the body 1716 to the body plate 1784. In the illustrated embodiment, the male portion 1780 of a coupling 1782 is a T-shaped protrusion extending radially from the cylindrical wall 1724 of the body 1716 and the female portion 1786 of the coupling 1782 is a slot formed horizontally in the body plate 1784. The T-shaped protrusion is inserted through the slot and the body plate is rotated ninety degrees to couple the body 1716 to the body plate 1784. When the retaining collar 1710 is fully assembled, the caps 1755 engage the T-shaped protrusion and prevent the body 1716 from rotating relative to the body plate 1784. It is within the scope of the disclosure for other common forms of couplings to be utilized to couple the body 1716 to the body plate 1784.

After attaching the body 1716 to the body plate 1784, the shafts 1751 of the modular guide bushings 1720 are inserted into the guide slot 1658 of the guide plate 1610 and the retaining collar 1710 is assembled. The caps 1755 of the modular guide bushings 1720 are attached to the shafts 1751 of the modular guide bushings 1720 and fasteners 1790 are inserted through the outer plate 1788, the modular bushings 1720 and the body plate 1784 to complete the assembly of the retaining collar 1710. In the illustrated embodiment, fastener holes are provided in the outer plate 1788, the modular bushings 1720 and the body plate 1784 to facilitate assembly of the retaining collar 1710.

When so assembled, the guide bushings 1720 extend perpendicularly from the longitudinal axis of the body 1716 of the retaining collar 1710. The guide bushings 1720 define a plane parallel to the top wall 1726 of the retaining collar 1710. When the shafts 1751 of the guide bushings 1720 are extended through the guide slot 1658 to couple the retaining collar 1710 to the guide 1610, the inner walls of the heads 1749 of the guide bushings 1720 are closely adjacent to, or in engagement with, the outer wall 1656 of the guide 1610. When so coupled to the guide 1610, the outer walls of the caps 1755 of the guide bushings 1720 are adjacent to, or in engagement with, the inner wall 1654 of the guide 1610. Illustratively, the shafts 1751 of the anterior guide bushing 1748 and the posterior guide bushing 1750 ride on the convex bottom wall 1662 of the guide slot 1658 and ride against the concave top wall 1660 of the guide slot 1658 when the retaining collar 1710 is reciprocated posteriorly-anteriorly. Thus, inner walls of the heads 1749 of the guide bushings 1720 and the outer wall 1656 of the guide 1610, the outer walls of the caps 1755 of the guide bushings 1720 of the retaining collar 1710 and the inner wall 1654 of the guide 1610, the shafts 1751 of the guide bushings 1720 and the convex bottom wall 1662 and concave top wall 1660 of the guide slot 1658 cooperate to maintain the proper alignment of the cutting tool 1704 during resection of the bone.

Illustratively, guide bushings 1720 act as track followers configured to induce the retaining collar 1710 to follow a path having a curvature conforming to the curvature of the concave top wall 1660 and convex bottom wall 1662 of the guide slot 1658. Those skilled in the art will recognize that other track following devices may be utilized within the scope of the disclosure including, but not limited to walls, bosses, ears, and flanges extending from the body 1716 of the retaining collar 1710 and configured to engage and be guided by the concave top wall 1660 and convex bottom wall 1662 of the guide slot 1658.

One embodiment of a uni-compartmental knee replacement procedure appropriate for utilization of the disclosed bone shaping tools begins with the surgeon performing an antero-medial or antero-lateral skin incision. The incision should begin 1 cm proximal to the superior border of the patella. It should extend 6 to 10 cm distally along the edge of the patella and patella tendon, and end 2 cm distal to the joint line. A longer incision is may be advised when first starting to use the procedure or if the patient is obese.

The surgeon then enters the joint capsule with a parapatellar incision. Once the joint is exposed, may make a final assessment of the extent of arthritic damage and the suitability of the joint for this procedure. The surgeon reflects the deep menisco-tibial layer of the medial or lateral capsule to provide good access to any tibial osteophytes and allow accurate wound closure. The surgeon also excises any excess deep synovium to provide clear sight of the joint. If required, all or part of the fat pad may also be excised to improve vision and allow inspection of the opposite compartment.

Retractors may be introduced to maintain access to the joint at all stages of the procedure. No ligament releases should be necessary. In order to achieve medial/lateral (M/L) alignment and joint stability, all osteophytes should be removed from the entire medial or lateral edges of the femur and tibia. A retractor is used on the patella rim to draw the patella into a central position.

Next the surgeon proceeds to the tibial resection of the UKR procedure. The knee is placed in 90 degrees of flexion to perform the tibial resection. A tibial alignment guide, such as the Preservation Tibial Cutting Block, Cat. No. 2498-60-002, 004 available from DePuy may be utilized in performing the tibial resection. The tibial cutting block of such an alignment guide should be raised to just below the level of the joint line.

When a medial UKR procedure is being performed, the tibial cutting block is now positioned 2 mm medial to the center of the tibial tubercle. M/L adjustment is made proximally to achieve varus/valgus alignment that is perpendicular to the mechanical axis of the tibia. The A/P slope of the tibia is then set using the anterior crest of the tibia as a reference.

The posterior tibial slope is adjusted to approximately 3 degrees to 5 degrees or to the figure determined from presurgical templating with a lateral X-ray.

The inferior/superior and A/P slope is then fixed. The surgeon then makes an L-cut using a reciprocating saw, using anatomic landmarks as reference points. For a medial Uni, make the L-cut should be made just lateral to the lateral border of the medial femoral condyle. The L-Cut is aligned in the sagittal plane using the midpoint of the lateral border of the insertion of the ACL as a landmark.

The surgeon then makes a transverse cut in the tibia in the proper orientation using a saw blade attached to an oscillating saw. The resected tibial bone chip is then removed.

The resection of the medial condyle of the femur may be accomplished with or without an initial distal femoral resection. If the initial distal femoral resection is utilized, the alignment guide from the PRESERVATION™ system may be used in accordance with procedures recommended for its use. With the leg held in full extension, the alignment guide and extramedullary alignment rod are assembled into the slot of the distal femoral cutting block to check overall alignment. Varus/valgus alignment can be assessed in the frontal plane. Neutral position of the distal femoral cut can be verified, from the lateral view. An oscillating saw is utilized to perform distal femoral cut. The bone removed from the distal femur is minimal. Once the resected distal bone is removed, any remaining soft tissue is cleared from the meniscal rim and posterior tibia.

Utilization of an initial distal femoral cut permits the femoral size established during preoperative templating to be checked using a femoral rotation and sizing guide in a known manner. The anterior tip profile and M/L width of the guide is the same as the femoral prosthesis. The aim is to ensure a smooth transition of the patella from the trochlea onto the anterior tip of the femoral prosthesis and avoid implant overhang. A femoral component is selected that covers the distal femoral cartilage erosion without overhanging the patello femoral joint. If between sizes, the smaller of the two is generally chosen.

To facilitate rotation of the anterior aspect of the femur, make a longitudinal mark on the condyle in full extension, indicating the central MIL articulating point of the femur over the tibial plateau. Aligning the anterior tip of the guide with this mark will help verify proper femoral alignment. It is also important to avoid femoral component overhang on the anterior aspect of the femur. Once the appropriate femoral component is selected, the guide 10 and guided cutting tool 100, 200 corresponding with the selected component is assembled prior to being attached to the femur.

The guide is positioned and aligned on the femoral component using the following steps: (1) With the knee placed in flexion, the guide is positioned with the anterior foot seated proximally of the load bearing portion of the anterior condyle. (2) The guide 10 is positioned in the correct medial-lateral and rotational position (along the distal weight bearing surface) to obtain maximum femoral coverage. The track of the guide 10 replicates the outer medial-lateral geometry of the femoral implant. (3) Ensure the guide is rotated correctly for femoral alignment. The femoral implant provides a 7° anatomic angle, between the distal and posterior surfaces, which should closely replicate the geometry of the anatomic femur. (4) Determine the proper varus/valgus positioning of the guide 10 by ensuring that the tangent line at the center of the guide 10 is perpendicular to the long axis of the femur.

Alternatively, if CAS technology is available, it may be utilized to accurately position the guide by based upon the registered geometry of the bone. Those skilled in the art will be familiar with the techniques registering when a CAS system utilized.

With the guide correctly positioned, the guide 10 is pinned in place with 0.125" (3.2 mm) headless fixation pins through both the holes 29 in the anterior lateral ear and posterior medial ear, as shown, for example, in FIGS. 8-11. An additional pin is placed in the hole 29 provided in central medial ear of the guide 10 to ensure it remains stable during resection of the posterior condyle. For hard or sclerotic bone, it may be necessary to pre-drill the holes with the 0.125" (3.2 mm) quick disconnect drill bits. Additional stabilization pins may be placed in the holes 29 left vacant by the guide. It may be necessary to utilize a high speed burr to remove the hard layer of sclerotic bone prior to using the cutter.

The power source should be started prior to plunging the end-mill into the bone to avoid chipping and gouging. After initial bone engagement, the end-mill is plunged into the bone three to four times down the length of the guide. The end-mill is then used in a sweeping motion to clear our remaining bone (end-mill blades are both side-cutting and end-cutting). The depth stop 102 coming into contact with the retaining collar will automatically stop the progress of the end-mill when it reaches the appropriate depth.

The appropriate level of preparation is complete when the depth stop comes into contact with the retaining collar as it is moved along its entire path of travel. It is critical that this is completed along the entire path of travel for the implant to fit properly.

Final preparatory steps can be performed to add any necessary features such as peg or keel shapes. The same guide rails would be used to guide the necessary preparatory instruments such as a drill or burr.

Although specific embodiments of the invention have been described herein, other embodiments may be perceived by those skilled in the art without departing from the scope of the invention as defined by the following claims. For example, although the invention has been described in terms of the implantation of the femoral portion of a knee prosthesis, it can be used with prostheses for other joints such as the shoulder, hip, or elbow.

What is claimed is:

1. A bone resection tool for resecting a portion of a bone, comprising:
    a guide configured to be removably attached at a fixed position above an end portion of a bone, the guide including a track with a curvature corresponding to a curved surface of a prosthetic device;
    a cutting tool including a cutting face;
    a track follower configured to reciprocate between a first part of the track and a second part of the track, and to rotatably couple to the cutting tool; and
    a depth stop configured to position the cutting face at a location below the track at a plurality of distances;
    wherein the cutting tool includes a shaft having the cutting face positioned at one end thereof;
    wherein the track follower includes a retaining collar having an opening in which the shaft is slidably received such that the cutting face is positioned below the track; and
    wherein the depth stop includes an opening in which the shaft is slidably received and at least one fastener configured to releasably secure the depth stop at one of a plurality of positions along a longitudinal axis of the shaft of the cutting tool, the depth stop positioned above the retaining collar such that the depth stop is rotatable with the shaft about the longitudinal axis of the shaft and contact between the depth stop and the retaining collar prevents movement of the cutting face of the shaft in a direction towards the bone.

2. The bone resection tool of claim 1, the depth stop being and the retaining collar being configured to maintain the shaft of the cutting tool substantially perpendicular to the track.

3. The bone resection tool of claim 1, wherein the at least one fastener comprises at least one set screw.

4. A method for resecting an end of a bone, the method comprising:

removably attaching a guide at a fixed position above an end portion of a bone, the guide including a track with a curvature corresponding to a curved surface of a prosthetic device;

placing a track follower in the track for reciprocation between a first part of the track and a second part of the track;

rotatably coupling a cutting tool including a cutting face to the track follower; and fixedly positioning the cutting face at a location below the track at any one of a plurality of distances using a depth stop;

wherein the cutting tool further comprises a shaft having the cutting face at one end thereof, the shaft extending though a retaining collar of the track follower so that the cutting face is positioned below the track; and wherein the positioning of the cutting face further comprises:

fixing the depth stop at one of a plurality of different positions along a longitudinal axis of the shaft above the track such that the depth stop is rotatable with the shaft; and moving the shaft longitudinally toward the bone until the depth stop contacts the retaining collar.

5. The method of claim 4, further comprising:

reciprocating the cutting tool in the track to cause the cutting face to resect the end portion of the bone such that the end portion of the bone exhibits the curvature once the cutting face is positioned at one of the distances below the track.

6. The bone resection tool of claim 5, wherein the reciprocation of the cutting tool further comprises:

maintaining the shaft of the cutting tool substantially perpendicular to the curvature of the track during the reciprocation.

7. A bone resection tool for resecting a portion of a bone, comprising:

a guide configured to be removably attached at a fixed position above an end portion of a bone, the guide including a track with a curvature corresponding to a curved surface of a prosthetic device;

a cutting tool including a shaft and a cutting face, the cutting face positioned at one end of the shaft;

a retaining collar slidably and rotatably supporting the shaft of the cutting tool with the cutting face positioned below the track, the retaining collar including guide pins that interact with the track to enable the retaining collar to reciprocate between a first part of the track and a second part of the track while maintaining the shaft perpendicular to a tangent of the curvature of the track; and a depth stop positioned above the retaining collar, the depth stop releasably secured to the shaft at one of a plurality of positions along a longitudinal axis of the shaft above the track such that the depth stop is rotatable with the shaft and configured to contact the retaining collar to prevent movement of the cutting face toward the bone.

8. The bone resection tool of claim 7, wherein the retaining collar and the depth stop each include an opening for slidably receiving the shaft of the cutting tool, the depth stop including at least one fastener for releasably securing the depth stop at the one of the plurality of positions along the longitudinal axis of the shaft.

* * * * *